(12) United States Patent
Zysk et al.

(10) Patent No.: US 7,787,129 B2
(45) Date of Patent: Aug. 31, 2010

(54) METHOD AND APPARATUS FOR MEASUREMENT OF OPTICAL PROPERTIES IN TISSUE

(75) Inventors: Adam M. Zysk, Chicago, IL (US); Steven G. Adie, Belmont, WA (US); Matthew S. Leigh, Carlisle, WA (US); Julian J. Armstrong, Carlisle, WA (US); David D. Sampson, Fremantle, WA (US); Stephen A. Boppart, Champaign, IL (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 629 days.

(21) Appl. No.: 11/669,561

(22) Filed: Jan. 31, 2007

(65) Prior Publication Data
US 2007/0203404 A1 Aug. 30, 2007

Related U.S. Application Data

(60) Provisional application No. 60/764,178, filed on Jan. 31, 2006.

(51) Int. Cl.
*G01B 9/02* (2006.01)
(52) U.S. Cl. .................................. 356/481; 356/517
(58) Field of Classification Search ................ 356/477, 356/479, 481, 482, 517, 498, 454; D24/138
See application file for complete search history.

(56) References Cited

U.S. PATENT DOCUMENTS

| 4,522,811 A | 6/1985 | Eppstein et al. |
| 4,930,516 A | 6/1990 | Alfano et al. |
| 5,095,487 A | 3/1992 | Meyerhofer et al. |
| 5,199,431 A | 4/1993 | Kittrell et al. |
| 5,247,343 A | 9/1993 | Burch |
| 5,280,788 A | 1/1994 | Janes et al. |
| 5,303,710 A | 4/1994 | Bashkansky et al. |

(Continued)

FOREIGN PATENT DOCUMENTS

EP 1 154 224 11/2001

(Continued)

OTHER PUBLICATIONS

Ai et al., "Electrostatic layer-by-layer nanoassembly on biological microtemplates: platelets", Biomacromolecules, 3:560-564, 2002.

(Continued)

*Primary Examiner*—Tarifur Chowdhury
*Assistant Examiner*—Jonathan M Hansen
(74) *Attorney, Agent, or Firm*—Evan Law Group LLC

(57) ABSTRACT

A method of analyzing tissue includes inserting a radiation source into tissue, impinging radiation upon the tissue, obtaining a sample signal of the radiation that impinges upon the tissue, and determining a refractive index of the tissue from the sample signal. The method may also include determining at least one other optical property of the tissue. The method may provide for identifying tissue as part of a biopsy method. A device for analyzing tissue may include a low-coherence interferometer and a probe optically coupled to the interferometer, where the probe includes a radiation source.

28 Claims, 11 Drawing Sheets

U.S. PATENT DOCUMENTS

| | | | |
|---|---|---|---|
| 5,362,478 A | 11/1994 | Desai et al. | |
| 5,439,686 A | 8/1995 | Desai et al. | |
| 5,451,785 A | 9/1995 | Faris | |
| 5,459,570 A | 10/1995 | Swanson et al. | |
| 5,491,524 A | 2/1996 | Hellmuth et al. | |
| 5,498,421 A | 3/1996 | Grinstaff et al. | |
| 5,505,932 A | 4/1996 | Grinstaff et al. | |
| 5,508,021 A | 4/1996 | Grinstaff et al. | |
| 5,512,268 A | 4/1996 | Grinstaff et al. | |
| 5,560,933 A | 10/1996 | Soon-Shiong et al. | |
| 5,635,207 A | 6/1997 | Grinstaff et al. | |
| 5,639,473 A | 6/1997 | Grinstaff et al. | |
| 5,648,506 A | 7/1997 | Desai et al. | |
| 5,650,156 A | 7/1997 | Grinstaff et al. | |
| 5,665,382 A | 9/1997 | Grinstaff et al. | |
| 5,665,383 A | 9/1997 | Grinstaff et al. | |
| 5,752,518 A | 5/1998 | McGee et al. | |
| 5,836,877 A | 11/1998 | Zavislan | |
| 5,891,619 A | 4/1999 | Zakim et al. | |
| 5,914,806 A | 6/1999 | Gordon, II et al. | |
| 5,921,926 A | 7/1999 | Rolland et al. | |
| 5,930,026 A | 7/1999 | Jacobson et al. | |
| 5,972,493 A | 10/1999 | Iwasaki et al. | |
| 5,994,690 A | 11/1999 | Kulkarni et al. | |
| 5,995,645 A | 11/1999 | Soenksen et al. | |
| 6,002,476 A | 12/1999 | Treado | |
| 6,002,480 A | 12/1999 | Izatt et al. | |
| 6,037,579 A | 3/2000 | Chan et al. | |
| 6,068,600 A | 5/2000 | Johnson et al. | |
| 6,069,932 A | 5/2000 | Peshkin et al. | |
| 6,091,496 A | 7/2000 | Hill | |
| 6,108,081 A | 8/2000 | Holtom et al. | |
| 6,111,645 A | 8/2000 | Tearney et al. | |
| 6,134,003 A | 10/2000 | Tearney et al. | |
| 6,151,522 A | 11/2000 | Alfano et al. | |
| 6,156,292 A | 12/2000 | Quay | |
| 6,159,445 A | 12/2000 | Klaveness et al. | |
| 6,167,297 A | 12/2000 | Benaron | |
| 6,208,886 B1 | 3/2001 | Alfano et al. | |
| 6,219,137 B1 | 4/2001 | Vo-Dinh | |
| 6,231,834 B1 | 5/2001 | Unger et al. | |
| 6,246,892 B1 | 6/2001 | Chance | |
| 6,246,901 B1 | 6/2001 | Benaron | |
| 6,249,271 B1 | 6/2001 | Albert et al. | |
| 6,262,706 B1 | 7/2001 | Albert et al. | |
| 6,262,833 B1 | 7/2001 | Loxley et al. | |
| 6,264,917 B1 | 7/2001 | Klaveness et al. | |
| 6,264,918 B1 | 7/2001 | Johnson et al. | |
| 6,280,704 B1 | 8/2001 | Schutt et al. | |
| 6,300,932 B1 | 10/2001 | Albert | |
| 6,307,633 B1 | 10/2001 | Mandella et al. | |
| 6,307,634 B2 | 10/2001 | Hitzenberger et al. | |
| 6,312,304 B1 | 11/2001 | Duthaler et al. | |
| 6,315,981 B1 | 11/2001 | Unger | |
| 6,344,272 B1 | 2/2002 | Oldenburg et al. | |
| 6,363,163 B1 | 3/2002 | Xu et al. | |
| 6,428,811 B1 | 8/2002 | West et al. | |
| 6,485,413 B1* | 11/2002 | Boppart et al. | 600/160 |
| 6,514,767 B1 | 2/2003 | Natan | |
| 6,529,277 B1 | 3/2003 | Weitekamp | |
| 6,530,944 B2 | 3/2003 | West et al. | |
| 6,538,805 B1 | 3/2003 | Norwood et al. | |
| 6,539,156 B1 | 3/2003 | Dickson et al. | |
| 6,560,478 B1 | 5/2003 | Alfano et al. | |
| 6,564,087 B1 | 5/2003 | Pitris et al. | |
| 6,574,401 B2 | 6/2003 | Neuberger et al. | |
| 6,584,335 B1 | 6/2003 | Haar et al. | |
| 6,615,063 B1 | 9/2003 | Ntziachristos et al. | |
| 6,618,423 B1 | 9/2003 | Dekorsy et al. | |
| 6,689,067 B2 | 2/2004 | Sauer et al. | |
| 6,690,966 B1 | 2/2004 | Rava et al. | |
| 6,795,777 B1 | 9/2004 | Scully et al. | |
| 6,825,928 B2 | 11/2004 | Liu et al. | |
| 6,839,586 B2 | 1/2005 | Webb | |
| 6,922,583 B1 | 7/2005 | Perelman et al. | |
| 7,181,266 B2 | 2/2007 | Frangioni et al. | |
| 7,198,777 B2 | 4/2007 | Boppart et al. | |
| 7,217,410 B2 | 5/2007 | Suslick et al. | |
| 7,610,074 B2 | 10/2009 | Boppart et al. | |
| 2002/0028993 A1 | 3/2002 | Hainfeld | |
| 2002/0054912 A1 | 5/2002 | Kim et al. | |
| 2002/0087071 A1 | 7/2002 | Schmitz et al. | |
| 2002/0168161 A1 | 11/2002 | Price et al. | |
| 2003/0045798 A1 | 3/2003 | Hular et al. | |
| 2003/0068496 A1 | 4/2003 | Wei et al. | |
| 2003/0082104 A1 | 5/2003 | Mertelmeier | |
| 2003/0171678 A1 | 9/2003 | Batten et al. | |
| 2004/0015062 A1 | 1/2004 | Ntziachristos et al. | |
| 2004/0023415 A1 | 2/2004 | Sokolov et al. | |
| 2004/0024307 A1 | 2/2004 | Golman et al. | |
| 2004/0058458 A1 | 3/2004 | Anker et al. | |
| 2004/0186359 A1 | 9/2004 | Beaudoin et al. | |
| 2004/0249268 A1 | 12/2004 | Da Silva | |
| 2005/0004453 A1 | 1/2005 | Tearney et al. | |
| 2005/0036150 A1 | 2/2005 | Izatt et al. | |
| 2005/0078363 A1 | 4/2005 | Gugel | |
| 2005/0149002 A1 | 7/2005 | Wang et al. | |
| 2005/0168735 A1 | 8/2005 | Boppart et al. | |
| 2005/0171433 A1 | 8/2005 | Boppart et al. | |
| 2005/0254057 A1* | 11/2005 | Alphonse | 356/479 |
| 2006/0039004 A1 | 2/2006 | De Boer et al. | |
| 2006/0066848 A1 | 3/2006 | Frankel | |
| 2006/0109478 A1 | 5/2006 | Tearney et al. | |
| 2006/0192969 A1 | 8/2006 | Marks et al. | |
| 2006/0281068 A1 | 12/2006 | Maier et al. | |
| 2006/0285635 A1 | 12/2006 | Boppart et al. | |
| 2006/0292839 A1 | 12/2006 | Yi et al. | |
| 2007/0203404 A1 | 8/2007 | Zysk et al. | |
| 2008/0140341 A1 | 6/2008 | Ralston et al. | |
| 2008/0281205 A1 | 11/2008 | Naghavi et al. | |
| 2009/0185166 A1 | 7/2009 | Oldenburg et al. | |
| 2009/0185191 A1 | 7/2009 | Boppart et al. | |
| 2009/0221920 A1 | 9/2009 | Boppart et al. | |

FOREIGN PATENT DOCUMENTS

| | | |
|---|---|---|
| EP | 1 312 912 | 5/2003 |
| EP | 1 447 043 | 8/2004 |
| EP | 0 963 540 | 3/2006 |
| WO | WO 90/01697 | 2/1990 |
| WO | WO 97/32182 | 9/1997 |
| WO | WO98/30873 | 7/1998 |
| WO | WO 98/38907 | 9/1998 |
| WO | WO99/06794 | 2/1999 |
| WO | WO99/58972 | 11/1999 |
| WO | WO 00/42906 | 7/2000 |
| WO | WO 00/42912 | 7/2000 |
| WO | WO02/41760 | 5/2002 |
| WO | WO 02/088705 | 11/2002 |
| WO | WO03/061454 | 7/2003 |
| WO | WO2005/028663 | 3/2005 |
| WO | WO2006/020302 | 2/2006 |
| WO | WO2006/032009 | 3/2006 |
| WO | WO2006/099191 | 9/2006 |
| WO | WO2006/135628 | 12/2006 |
| WO | WO 07/027194 | 3/2007 |
| WO | WO 07/090147 | 9/2007 |
| WO | WO 2008/008774 | 1/2008 |

OTHER PUBLICATIONS

Amsden et al., "An examination of factors affecting the size, distribution, and release characteristics of polymer microbeads made using electrostatics", J. Control. Release, 43:183-196, 1997.

Amsden, "The production of uniformly sized polymer microspheres", Pharm. Res., 16:1140-1143, 1999.

Balasubramanian et al., "Extraction and dispersion of large gold nanoparticles in nonpolar solvents", J. Dispers. Sci. Tech. 22:485-89, 2001.

Balasubramanian et al., "Dispersion and stability studies of resorcinarene-encapsulated gold nanoparticles", Langmuir, 18:3676-81, 2002.

Barton et al., "Use of microbubbles as an optical coherence tomography contrast agent", Acad. Radiol, 9, (Suppl 1):552-555, 2002.

Blackwell et al., "New approaches to olefin cross-metathesis", J. Am. Chem. Soc., 122:58-71, 2000.

Boppart et al., "Imaging Developing Neural Morphology Using Optical Coherence Tomography", J. Neuroscience Methods, vol. 70, pp. 65-72, 1996.

Boppart et al., "Investigation of Developing Embryonic Morphology Using Optical Coherence Tomography", Developmental Biology, vol. 177, pp. 54-63, 1996.

Boppart et al., "Noninvasive assessment of the developing Xenopus cardiovascular system using optical coherence tomography", Proc. Natl. Acad. Sci. USA, 94: 4256-4261, 1997.

Boppart et al., "Forward-Imaging Instruments for Optical Coherence Tomography", Optics Letters, vol. 22, No. 21, pp. 1618-1620, 1997.

Boppart et al., "In vivo Cellular Optical Coherence Tomography Imaging", Nature Medicine, vol. 4, No. 7, pp. 861-865, 1998.

Boppart et al., "Intraoperative Assessment of Microsurgery with Three-Dimensional Optical Coherence Tomography", Radiology, vol. 208, pp. 81-86, 1998.

Boppart et al., "Optical Coherence Tomography for Neurosurgical Imaging of Human Intracortical Melanoma", Neurosurgery, vol. 43, No. 4, pp. 834-841, 1998.

Boppart, "Surgical Diagnostics, Guidance, and Intervention Using Optical Coherence Tomography", Ph.D. Thesis, Massachusetts Institute of Technology, Cambridge, MA, 226 pages, 1998.

Boppart et al., "High-Resolution Optical Coherence Tomography-Guided Laser Ablation of Surgical Tissue", J. Surgical Research, 82:275-84, 1999.

Boppart, "Endoscopic Optical Coherence Tomography Imaging of Barrett's Esophagus", M.D. Thesis, Harvard University, 2000.

Bouma et al., "High resolution optical coherence tomographic imaging using a mode-locked $Ti:Al_2O_3$ laser source", Optics Letter, 20:1486-1488, 1995.

Bouma et al., "High-resolution imaging of the human esophagus and stomach in vivo using optical coherence tomography", Gastrointestinal Endoscopy, 51: 467-474, 2000.

Boyer et al., "Photothermal Imaging of Nanometer-Sized Metal Particles Among Scatterers", Science, 297:1160-63, 2002.

Brezinski et al., "Optical Coherence Tomography for Optical Biopsy: Properties and Demonstration of Vascular Pathology", Circulation, vol. 93, pp. 1206-1213, 1996.

Bugaj et al., "Novel fluorescent contrast agents for optical imaging of in vivo tumors based on a receptor-targeted dye-peptide conjugate platform", J. Biomedical Optics, 6:122-33, 2001.

Burns et al., "Tumor-localizing and photosensitizing properties of hematoporphyrin derivative in hamster buccal pouch carcinoma", Oral Surg. Oral Med. Oral Pathol., 61:368-372, 1986.

Cain et al., "Thresholds for Visible Lesions in the Primate Eye Produced by Ultrashort Near-Infrared Laser Pulses", Investigative Ophthalmology & Visual Science, 40:2343-49, 1999.

Cain et al., "Visible Retinal Lesions from Ultrashort Laser Pulses in the Primate Eye", Investigative Ophthalmology & Visual Science, 36:879-888, 1995.

Caruso et al., "Nanoengineering of inorganic and hybrid hollow spheres by colloidal templating", Science, 282:1111-1114, 1998.

Cepak et al., "Preparation and Stability of Template-Synthesized Metal Nanorod Sols in Organic Solvents", J. Phys. Chem. B, 102:9985-90, 1998.

Chen et al., "Noninvasive Imaging of In Vivo Blood Flow Velocity Using Optical Doppler Tomography", Optics Letters, vol. 22, pp. 1119-1121, 1997.

Christiansen et al., "Physical and biochemical characterization of Albunex™, a new ultrasound contrast agent consisting of air-filled albumin microparticles suspended in a solution of human albumin", Biotechnol. Appl. Biochem., 19:307-20, 1994.

Clark et al., "Second harmonic generation properties of fluorescent polymer-encapsulated gold nanoparticles", J. Am. Chem. Soc., 122:10234-35, 2000.

de Boer et al., "Two-Dimensional Birefringence Imaging in Biological Tissue by Polarization-Sensitive Optical Coherence Tomography", Optics Letters, vol. 22, pp. 934-936, 1997.

Decher "Fuzzy Nanoassemblies: Toward Layered Polymeric Multicomposites", Science, 277:1232-1237, 1997.

Desai et al., "Controlled and targeted drug delivery with biocompatible protein shell microspheres", 20th Annual Meeting of Society of Biomaterials, Apr. 4-9, 1994, Boston, MA: Proc. Soc. Biomaterial, 20:112, 1994.

Dick et al., "Computed tomography of experimental liver abscesses using a new liposomal contrast agent", Investigative Radiology, 31:194-203, 1996.

Dowlatshahi et al., "Histologic Evaluation of Rat Mammary Tumor Necrosis By Interstitial Nd:YAG Laser Hyperthermia", Lasers in Surgery and Medicine, 12:159-164, 1992.

Drexler et al., "In vivo Ultrahigh-Resolution Optical Coherence Tomography", Optics Letters, vol. 24, No. 17, pp. 1221-1223, 1999.

El-Sayed "Some interesting properties of metals confined in time and nanometer space of different shapes", Accounts of Chemical Research, 34:257-64, 2001.

Freeman et al., "Self-Assembled Metal Colloid Monolayers: An Approach to SERS Substrates", Science, 267:1629-1632, 1995.

Fu et al., "Visual evidence of acidic environment within degrading poly(lactic-co-glycolic acid) (PLGA) microspheres", Pharmaceutical Research, 17:100-106, 2000.

Fujimoto et al., "Optical biopsy and imaging using optical coherence tomography", Nature Medicine, 1:970-972, 1995.

Gazelle et al., "Nanoparticulate computed tomography contrast agents for blood pool and liver-spleen imaging", Acad. Radiol., 1:373-376, 1994.

Geny et al., "Safety of a new transpulmonary echocontrast agent (Albunex®) in repeated echocardiographic studies in patients", Clin. Cardiol., 20:111-115, 1997.

Gimenez-Conti et al., "The hamster cheek pouch carcinogenesis model", J. Cellular Biochemistry Supplement, 17F:83-90, 1993.

Gram, "Drug absorption and distribution", in Modern Pharmacology with Clinical Applications $5^{th}$ Ed., Craig et al., eds., Little, Brown, & Co., Inc.; Boston, MA, pp. 13-24, 1997.

Grinstaff et al., "Air-filled proteinaceous microbubbles: synthesis of an echo-contrast agent", Proc. Natl. Acad. Sci. USA, 88:7708-7710, 1991.

Grubbs et al., "Ring-Closing Metathesis and Related Processes in Organic Synthesis", Acc. Chem. Res., 28:446-52, 1995.

Haes et al., "A nanoscale optical biosensor: sensitivity and selectivity of an approach based on the localized surface plasmon resonance spectroscopy of triangular silver nanoparticles", J. Am. Chem. Soc., 124:10596-604, 2002.

Handley et al., "Colloidal gold labeling studies related to vascular and endothelial function, hemostasis and receptor-mediated processing of plasma macromolecules", European J. Cell Biology, 43:163-74, 1987.

Handley et al., "Colloidal gold-low density lipoprotein conjugates as membrane receptor probes", Proc. Natl. Acad. Sci. USA, 78:368-71, 1981.

Handley "Methods for Synthesis of Colloidal Gold", Colloidal Gold: Principles, Methods, and Applications, (Academic Press), vol. 1, pp. 13-32, 1989.

Hardikar et al., "Coating of nanosize silver particles with silica", J. Colloid and Interface Science, 221:133-36, 2000.

Harrington et al., "Gene therapy for prostate cancer: current status and future prospects", J. Urology, 166:1220-33, 2001.

Hartl et al., "Ultrahigh-Resolution Optical Coherence Tomography Using Continuum Generation In An Air-Silica Microstructure Optical Fiber", Optics Letters, 26:608-610, 2001.

Hee et al., "Optical coherence tomography of the human retina", Arch. Ophthalmol. 113: 325-332, 1995.

Hiergeist et al., "Application of magnetite ferrofluids for hyperthermia", J. Magnetism and Magnetic Materials, 201:420-22, 1999.

Hirsch et al., "A Whole Blood Immunoassay Using Gold Nanoshells", Analytical Chemistry, 75:2377-2381, 2003.

Huang et al., "Optical Coherence Tomography", Science, 254: 1178-1181, 1991.

Jackson et al., "Silver Nanoshells:Variations in Morphologies and Optical Properties", J. Phys. Chem. B, 105:2743-46, 2001.

Jana et al., "Wet chemical synthesis of high aspect ratio cylindrical gold nanorods", J. Phys. Chem. B, 105:4065-67, 2001.

Jang et al., "Visualization of Coronary Atherosclerotic Plaques in Patients Using Optical Coherence Tomography: Comparison With Intravascular Ultrasound", J. American College of Cardiology, 39:604-609, 2002.

Jensen et al., "Electrodynamics of noble metal nanoparticles and nanoparticle clusters", J. Cluster Science, 10:295-317, 1999.

Jin et al., "Photoinduced conversion of silver nanospheres to nanoprisms", Science, 294:1901-03, 2001.

Jordan et al., "Magnetic fluid hyperthermia (MFH): Cancer treatment with AC magnetic field induced excitation of biocompatible superparamagnetic nanoparticles", Magnetism and Magnetic Materials., 201:413-19, 1999.

Jue et al., "Addition of sulfhydryl groups to *Escherichia coli* ribosomes by protein modification with 2-iminothiolane (methyl 4-mercaptobutyrimidate)", Biochemistry, 17:5399-5406, 1978.

Kempka et al., "Binding, uptake, and transcytosis of ligands for mannose-specific receptors in rat liver: an electron microscopic study", Experimental Cell Research,176, 38-48, 1988.

Keye et al., "Argon Laser Therapy of Endometriosis: A Review of 92 Consecutive Patients" Fertility and Sterility, 47:208-212, 1987.

Kim et al., "Hollow silica spheres of controlled size and porosity by sol-gel processing", J. Am. Ceram. Soc., 74:1987-1992, 1991.

Kim et al., "Photochemical synthesis of gold nanorods" J. Am. Chem. Soc., 124:14316-17, 2002.

Kim et al., "Self-Organization of Large Gold Nanoparticle Arrays", J. Am. Chem. Soc., 123:7955-56, 2001.

Kim et al., "Fabrication of hollow silica aerogel spheres by a droplet generation method and sol-gel processing" J. Vac. Sci., Technol. A., 7:1181-1184, 1989.

Kneipp et al., "Ultrasensitive Chemical Analysis by Raman Spectroscopy", Chem. Rev., 99:2957-75, 1999.

Kolb-Bachofen et al., "Electron microscopic evidence for an asialoglycoprotein receptor on Kupffer cells: localization of lectin-mediated endocytosis", Cell, 29:859-66, 1982.

Kolbeck, "The biomedical applications of protein microspheres", Ph.D. Doctoral Thesis, University of Illinois, Urbana-Champaign, title page and pp. 153, 159-160, 1999.

Korbelik et al., "Photofrin accumulation in malignant and host cell populations of various tumours", British Journal of Cancer, 73:506-513, 1996.

Langer "Drug delivery and targeting", Nature, 392:5-10, 1998.

Larson et al., "Water-Soluble Quantum Dots for Multiphoton Fluorescence Imaging in Vivo", Science, 300:1434-1436, 2003.

Lasic et al., "Liposomes revisited", Science, 267:1275-1276, 1995.

Lee et al., "Delivery of liposomes into cultured KB cells via folate receptor-mediated endocytosis", J. Biological Chemistry, 269:3198-3204, 1994.

Lee et al., "Engineered microsphere contrast agents for optical coherence tomography", Optics Letters, vol. 28, No. 17, pp. 1546-1548, 2003.

Lee et al., "Optical Characterization of Contrast Agents for Optical Coherence Tomography", Proceedings of SPIE, vol. 4967, pp. 129-134, 2003.

Leelarasamee et al., "A method for the preparation of polylactic acid microcapsules of controlled particle size and drug loading", J. Microencapsulation, 5:147-157, 1988.

Leitgeb et al., "Spectral measurement of absorption by spectroscopic frequency-domain optical coherence tomography", Optics Letters, 25:820-22, 2000.

Li et al., "Optical Coherence Tomography: Advanced Technology for the Endoscopic Imaging of Barrett's Esophagus", Endoscopy, vol. 32, pp. 921-930, 2000.

Li et al., "Imaging Needle for Optical Coherence Tomography", Optics Letters, 25:1520-1522, 2000.

Li et al., "On the growth of highly ordered pores in anodized aluminum oxide", Chem. Mater., 10:2470-80, 1998.

Li et al., "Polycrystalline nanopore arrays with hexagonal ordering on aluminum", J. Vac. Sci. Technol. A, 17:1428-31, 1999.

Licha, "Contrast agents for optical imaging", Topics in Current Chemistry, 222:1-29, 2002.

Lin et al. "Measurement of tissue optical properties by the use of oblique-incidence optical fiber reflectometry", Applied Optics, 36:136-43, 1997.

Lin et al., "Intraocular Microsurgery with a Picosecond Nd:YAG Laser", Lasers in Surgery and Medicine, 15:44-53, 1994.

Liu et al., "In vivo measurement of oxygen concentration using sonochemically synthesized microspheres", Biophysical J., 67:896-901, 1994.

Liu et al., "A novel two-step silica-coating process for engineering magnetic nanocomposites", Chem. Mater., 10:3936-40, 1998.

Liz-Marzan et al., "Homogeneous silica coating of vitreophobic colloids", Chem. Commun., 731-32, 1996.

Lvov et al., "Nanoparticle/polyion assembly on microtemplates (lipid tubules and latex spheres)", Colloids and Surfaces B: Biointerfaces, 23:251-256, 2002.

Lvov et al., "Thin film nanofabrication via layer-by-layer adsorption of tubule halloysite, spherical silica, proteins and polycations", Colloids and Surfaces A: Physicohem. Eng. Aspects, 198-200:375-382, 2002.

Marks et al., Nonlinear interferometric vibrational imaging, E-print@arxiv.org/physics/0311071, URL http://www.arxiv.org/abs/physics/0311071, pp. 1-5, 2003.

Marks et al., "Study of an Ultrahigh-Numerical-Aperture Fiber Continuum Generation Source For Optical Coherence Tomography", Optics Letters, 27:2010-2012, 2002.

Marks et al., "Pulse shaping strategies for nonlinear interferometric vibrational imaging optimized for biomolecular imaging", Conference Proceeding: EMBC 2004: 26th Annual International Conference of the Engineering in Medicine and Biology Society (Sept. 1-5, 2004, San Francisco, CA), vol. 2, 7 pages, (accession No. 8255487).

Masuda et al., "Ordered metal nanohole arrays made by a two-step replication of honeycomb structures of anodic alumina", Science, 268:1466-68, 1995.

Mathias et al., "Tumor-selective radiopharmaceutical targeting via receptor-mediated endocytosis of Gallium-67-deferoxamine-folate", J. of Nuclear Medicine, 37:1003-1008, 1996.

McNamara III et al., "Sonoluminescence temperatures during multibubble cavitation", Nature, 401:772-775,1999.

Micali et al., "Separation of Scattering and Absorption Contributions in UV/Visible Spectra of Resonant Systems", Anal. Chem., 73:4958-63, 2001.

Minton et al., "The Laser in Surgery. A 23 Year Perspective.", American Journal of Surgery, 151:725-729, 1986.

Mock et al., "Composite plasmon resonant nanowires", Nano Letters, 2:465-69, 2002.

Mock et al., "Shape effects in plasmon resonance of individual colloidal silver nanoparticles", J. Chem. Phys., 116:6755-59, 2002.

Mohwald, "From Langmuir monolayers to nanocapsules", Colloids and Surfaces A: Physicochem. Eng. Aspects, 171:25-31, 2000.

Morgner et al., "Spectrosopic optical coherence tomography", Optics Letters, 25:111-13, 2000.

Nicewarner-Peña et al. "Submicrometer metallic barcodes", Science, 294:137-41, 2001.

Nielsch et al., "Self-ordering regimes of porous alumina: the 10% porosity rule", Nano Letters 2:677-80, 2002.

Novak et al., "Purification of molecularly bridged metallic nanoparticle arrays by centrifugation and size exclusion chromatography", Anal. Chem., 73:5758-61, 2001.

Oldenburg et al., "Light Scattering From Dipole and Quadrupole Nanoshell Antennas", Appl. Phys. Lett., 75:1063-65, 1999.

Pasternack et al., "Resonance Light Scattering: A New Technique For Studying Chromophore Aggregation", Science, 269:935-39, 1995.

Pathak et al., "Detection of squamous neoplasia by fluorescence imaging comparing porfimer sodium fluorescence to tissue autofluorescence in the hamster cheek-pouch model", American Journal of Surgery, 170:423-426, 1995.
Peters, All about Albumin, in Biochemistry, Genetics, and Medical Applications, (Academic Press, New York), 3 pages, 1996.
Pinkerton et al., "Aerosolized fluorescent microspheres detected in the lung using confocal scanning laser microscopy", Microscopy Research and Technique, 26:437-443, 1993.
Pitris et al., "High-resolution imaging of gynecologic neoplasms using optical coherence tomography", Obstetrics & Gynecology, 93: 135-139, 1999.
Pitris et al., "Feasibility of optical coherence tomography for high-resolution imaging of human gastrointestinal tract malignancies", J. Gastroenterol., 35: 87-92, 2000.
Pollack et al., "Circumferential Argon Laser Photocoagulation for Prevention of Retinal Detachment", Eye, vol. 8, pp. 419-422, 1994.
Profio et al., "Transport of light in tissue in photodynamic therapy", Photochemistry and Photobiology, 46: 591-599, 1987.
Prudhomme et al., "Interstitial Diode Laser Hyperthermia in the Treatment of Subcutaneous Tumor", Lasers in Surgery and Medicine, 19:445-450, 1996.
Puliafito et al., "Imaging of macular disease with optical coherence tomography", Ophthalmology, 102: 217-229, 1995.
Puliafito et al., "Optical Coherence Tomography of Ocular Diseases", Slack Inc, Thorofare, N.J., pp. 3-34, 369-374, 1995.
Pusztay et al., "Encagement of Gold Nanoclusters in Crosslinked Resorcinarene Shells", Supramolecular Chemistry, 14:291-94, 2002.
Quaroni et al., "Preparation of Polymer-Coated Functionalized Silver Nanoparticles", J. Am. Chem. Soc., 121:10642-43, 1999.
Russell-Jones, "Use of vitamin $B_{12}$ conjugates to deliver protein drugs by the oral route", Critical Reviews in Therapuetic Drug Carrier Systems, vol. 15, No. 6, pp. 557-586, 1998.
Sadtler et al., "Spherical ensembles of gold nanoparticles on silica: electrostatic and size effects", Chem. Commun., 1604-05, 2002.
Sansdrap et al., "Influence of manufacturing parameters on the size characteristics and the release profiles of nifedipine from poly(DL-lactide-co-glycolide) microspheres", International Journal of Pharmaceutics, 98:157-164, 1993.
Schaefer et al., "Real-Time Digital Signal Processing-Based Optical Coherence Tomography and Doppler Optical Coherence Tomography", IEEE Transactions on Biomedical Engineering, vol. 51, No. 1, pp. 186-190, 2004.
Schaefer "Real-Time, Digital Signal Processing-Based Optical Coherence Tomography and Optical Doppler Tomography", Master Thesis, University of Illinois at Urbana-Champaign, 2001.
Schmitt et al., "Measurement of Optical Properties of Biological Tissues by Low-Coherence Reflectometry", Applied Optics., vol. 32, pp. 6032-6042, 1993.
Schmitt et al., "Subsurface Imaging of Living Skin with Optical Coherence Microscopy", Dermatology, vol. 191, pp. 93-98, 1995.
Schmitt et al., "Optical-coherence tomography of a dense tissue: statistics of attenuation and backscattering", Phys. Med. Biol., 39: 1705-1720, 1994.
Sergeev et al., "In vivo endoscopic OCT imaging of precancer and cancer states of human mucosa", Optics Express, 1: 432-440, 1997.
Sevick-Muraca et al., "Fluorescence-enhanced, near infrared diagnostic imaging with contrast agents", Current Opinion in Chemical Biology, Op. Chem. Biol., 6:642-50, 2002.
Shiga et al., "Preparation of Poly(D,L-lactide) and Copoly(lactide-glycolide) Microspheres of Uniform Size", J. Pharm. Pharmacol., 48:891-895, 1996.
Shipway et al., "Nanoparticle arrays on surfaces for electronic, optical, and sensor applications", ChemPhysChem., 1:18-52, 2000.
Sivak Jr. et al., "High-resolution endoscopic imaging of the GI tract using optical coherence tomography", Gastrointestinal Endoscopy, 51:474-479, 2000.
Slaga et al., "An animal model for oral cancer", J. National Cancer Institute Monographs, 13:55-60, 1992.
Sokolov et al., "Real-Time Vital Optical Imaging of Precancer Using Anti-Epidermal Growth Factor Receptor Antibodies Conjugated to Gold Nanoparticles", Cancer Research, 63:1999-2004, 2003.
Sönnichsen et al., "Drastic reduction of plasmon damping in gold nanorods", Physical Review Letters, vol. 88, No. 7:077402-1 to 077402-4, 2002.

Sönnichsen et al., "Spectroscopy of Single Metallic Nanoparticles Using Total Internal Reflection Microscopy", Appl. Phys. Lett., 77:2949-51, 2000.
Stavens et al., "Encapsulation of Neutral Gold Nanoclusters by Resorcinarenes", Langmuir, 15:8337-39, 1999.
Su et al., "Tumor characterization with dynamic contrast-enhanced MRI using MR contrast agents of various molecular weights", Magnetic Resonance in Medicine, 39:259-269, 1998.
Suslick et al., "Protein Microencapsulation of Nonaqueous Liquids", J. Am. Chem. Soc., 112:7807-7809, 1990.
Suslick et al., "Versatile sonochemical reaction vessels" in Experimental Organometallic Chemistry: A Practicum in Synthesis and Characterization, (A. Wayda, Darensburg MY, eds. ACS Symposium Series, Washington, D.C.), pp. 195-197, 1987.
Suslick, "Sonochemistry", Science, 247: 1439-1445, 1990.
Tanaka et al., "Direct visualization of colloidal gold-bound molecules and a cell-surface receptor by ultrahigh-resolution scanning electron microscopy", J. Microscopy, 161:455-61, 1991.
Tearney et al., "Optical Biopsy in Human Gastrointestinal Tissue Using Optical Coherence Tomography", American Journal of Gastroenterlogy, vol. 92, pp. 1800-1804, 1997.
Tearney et al., "Optical Biopsy in Human Urologic Tissue Using Optical Coherence Tomography", J. Urology, vol. 157, pp. 1915-1919 (reprinted as 11 pages), 1997.
Tearney et al., "Catheter-based optical imaging of a human coronary artery", Circulation, 94: 3013, 1996.
Tearney et al., "High-Speed Phase- and Group-Delay Scanning with a Grating-Based Phase Control Delay Line", Optics Letters, vol. 22, No. 23 :1811-1813, 1997.
Tearney et al., "In vivo endoscopic optical biopsy with optical coherence tomography", Science, 276: 2037-2039, 1997.
Tearney et al., "Rapid acquisition of in vivo biological images by use of optical coherence tomography", Optics Letters, 21: 1408-1410, 1996.
Tearney et al., "Scanning single-mode fiber optic catheter-endoscope for optical coherence tomography", Optics Letters, 21: pp. 543-545, 1996.
Templeton et al., "Monolayer-protected cluster molecules", Acc. Chem. Res., 33:27-36, 2000.
Timmerman et al., "Resorcinarenes" Tetrahedron, 52:2663-704, 1996.
Tkachenko et al., "Multifunctional Gold Nanoparticle-Peptide Complexes for Nuclear Targeting", J. Am. Chem. Soc., 125:4700-4701, 2003.
Toth et al., "Retinal effects of ultrashort laser pulses in the rabbit eye", Investigative Ophthalmology & Visual Science, 36:1910-17, 1995.
Toublan et al., "Magnetically-inducible optical contrast agents for optical coherence tomography", presented at the Optical Society of America Biomedical Topical Meeting, Miami, FL, Apr. 7-10, 2002.
Tripp et al., "Self-assembly of cobalt nanoparticle rings", J. Am. Chem. Soc., 124:7914-15, 2002.
Turkevich et al., "A Study of the Nucleation and Growth Processes in the Synthesis of Colloidal Gold", Faraday Soc., 11:55-75, 1951.
Tuting, "The immunology of cutaneous DNA immunization", Current Opinion in Molecular Therapeutics, vol. 1, No. 2, pp. 216-225, 1999.
Ung et al., "Controlled method for silica coating of silver colloids. Influence of coating on the rate of chemical reactions", Langmuir, 14:3740-48, 1998.
van der Laan et al., "In vitro activity of novel antifolates against human squamous carcinoma cell lines of the head and neck with inherent resistance to methotrexate", Int. J. Cancer, 51:909-914, 1992.
Van Der Smissen et al., "Ligand-induced clustering of asialoglycoprotein receptors on rat hepatocytes at 4° C", European J. of Cell Biology, 60:122-30, 1993.
Van Der Smissen et al., "Quantitative analysis of clustering on biological membranes: methodology and application to ligand-induced asialoglycoprotein receptor redistribution on rat hepatocytes", European J. of Cell Biology, 69:45-54, 1996.
van der Zande et al., "Colloidal dispersions of gold rods: synthesis and optical properties", Langmuir, 16:451-58, 2000.

Violante et al., "Improved detectability of VX2 carcinoma in the rabbit liver with contrast enhancement in computed tomography", Radiology, 134:237-239, 1980.

Vitkin et al., "Optical and thermal characterization of natural (*Sepia officinalis*) melanin", Photochemistry and Photobiology, 59:455-62, 1994.

Vo-Dinh, "Surface-Enhanced Raman Spectroscopy Using Metallic Nanostructures", Trends in Analytical Chemistry, 17:557-82, 1998.

Wang et al., "Semiconductor quantum dot-labeled microsphere bioconjugates prepared by stepwise self-assembly", Nano Lett., 2:857-861, 2002.

Wang et al., "Use of a Laser Beam with an Oblique Angle of Incidence to Measure the Reduced Scattering Coefficient of a Turbid Medium", Applied Optics, 34:2362-2366, 1995.

Webb et al., "Sonochemically produced fluorocarbon microspheres: a new class of magnetic resonance imaging agent", J. Magnetic Resonance Imaging, 6:675-683, 1996.

Wei et al., "Resorcinarene-encapsulated nanoparticles: building blocks for self-assembled nanostructures", J. Inclusion Phenomenal Macrocyclic Chemistry, 41, 83-86, 2001.

Wei et al., "Synthesis and Characterization of Resorcinarene-Encapsulated Nanoparticles", Mater. Res. Soc., Symp. Proc. Ser., 581:59-63, 1999.

Wei et al., "Tunable Surface-Enhanced Raman Scattering from Large Gold Nanoparticle Arrays", ChemPhysChem., 2:743-45, 2001.

Wong et al., "Sonochemically produced hemoglobin microbubbles", Mat. Res. Soc. Symp. Proc., 372:89-94, 1995.

Xu et al., "Electromagnetic Contributions to Single-Molecule Sensitivity in Surface-Enhanced Raman Scattering", Physical Review E, 62:4318-24, 2000.

Yazdanfar et al., "High Resolution Imaging of in vivo Cardiac Dynamics Using Color Doppler Optical Coherence Tomography", Optics Express, vol. 1, pp. 424-431, 1997.

Yguerabide et al., "Light-scattering submicroscopic particles as highly fluorescent analogs and their use as tracer labels in clinical and biological applications", Analytical Biochemistry, 262:137-56, 1998.

Yu et al., "Gold nanorods: electrochemical synthesis and optical properties", J. Phys. Chem. B, 101:6661-64, 1997.

Zaheer et al., "In vivo near-infrared fluorescence imaging of osteoblastic activity", Nature Biotechnology, 19:1148-54, 2001.

Marks et al., "Interferometric differentiation between resonant Coherent Anti-Stokes Raman Scattering and nonresonant four-wave-mixing processes", arXiv:physics/0403007, pp. 1-8, 2004.

Vinegoni et al., "Nonlinear optical contrast enhancement for optical coherence tomography", Optics Express, vol. 12, No. 2, p. 331-341, 2004.

Kee et al., "Simple approach to one-laser, broadband coherent anti-Stokes Raman scattering microscopy", Optics Letters, vol. 29, No. 23, p. 2701-2703, 2004.

Kano et al., "Vibrationally resonant imaging of a single living cell by supercontinuum-based multiplex coherent anti-Stokes Raman scattering microspectroscopy", Optics Express, vol. 13, Issue 4, pp. 1322-1327, 2005.

Gao et al., "Formulation, Characterization, and Sensing Applications of Transparent Poly(vinyl alcohol)-Polyelectrolyte Blends", Chem. Mater., 10, pp. 2481-2489, 1998.

Marks et al., Molecular Species Sensitive Optical Coherence Tomography Using Coherent Anti-Stokes Raman Scattering Spectroscopy, Coherence Domain Optical Methods and Optical Coherence Tomography In Biomedicine VII, Proceedings of SPIE, vol. 4956, pp. 9-13, 2003.

Bredfeldt et al., "Non-linear interferometric vibrational imaging", Conference on Lasers and Electro-optics, CLEO '03, pp. 309-311, 2003.

Vinegoni et al., "Nonlinear optical contrast enhancement for optical coherence tomography", http://www.arxiv.org/abs/physics/0312114, 13 pages (2003).

Zumbusch et al., "Three-dimensional vibrational imaging by coherent anti-Stokes Raman scattering", Phys. Rev. Lett., 82(20), pp. 4142-4145, 1999.

Cheng et al., "An epi-detected coherent anti-Stokes Raman scattering (E-CARS) microscope with high spectral resolution and high sensitivity", J. Phys. Chem, 105(7), pp. 1277-1280, 2001.

Hashimoto et al., "Molecular vibration imaging in the fingerprint region by use of coherent anti-Stokes Raman scattering microscopy with a collinear configuration", Opt. Lett., 25(24), pp. 1768-1770, 2000.

Volkmer et al., "Vibrational imaging with high sensitivity via epidected coherent anti-Stokes Raman scattering microscopy", Phys. Rev. Lett., 87(2):023901-1-4, 2001.

Schmitt et al., "Optical-coherence tomography of a dense tissue: statistics of attenuation and backscattering", Phys. Med. Biol., vol. 39, pp. 1705-1720, (1994).

Tearney et al., "In vivo endoscopic optical biopsy with optical coherence tomography", Science, vol. 276, pp. 2037-2039, (1997).

Fantini et al., "Assessment of the size, position, and optical properties of breast tumors in vivo by noninvasive optical methods", Applied Optics, vol. 37, pp. 1982-1989, 1998.

Faber et al., "Quantitative measurement of attenuation coefficients of weakly scattering media using optical coherence tomography", Optics Express, 12(19), pp. 4353-4365, 2004.

Fujimoto et al., "Optical Coherence Tomography: An Emerging Technology for Biomedical Imaging and Optical Biopsy", Neoplasia, 2(1-2), pp. 9-25, 2000.

Zysk et al., "Computational methods for analysis of human breast tumor tissue in optical coherence tomography images", Journal of Biomedical Optics, 11(5), 054015-1-054015-7, 2006.

Levitz et al., "Determination of optical scattering properties of highly-scattering media in optical coherence tomography images", Optics Express, 12(2), pp. 249-259, 2004.

Morgner et al., "Spectroscopic optical coherence tomography", Optics Letters, 25(2), pp. 111-113, 2000.

Gossage et al., "Texture analysis of optical coherence tomography images: feasibility for tissue classification", Journal of Biomedical Optics, 8(3), pp. 570-575, 2003.

Zvyagin et al., "Refractive index tomography of turbid media by bifocal optical coherence refractometry", Optics Express, 11(25), pp. 3503-3517, 2003.

Gottschalk, "Ein Meβverfahren zur Bestimmung der optischen Parameter biologisher Gewebe in vitro", Dissertation 93 HA 8984, Universität Fridericiana Karlsruhe, 1993.

Bolin, F.P. et al., "Refractive index of some mammalian tissues using a fiber optic cladding method", Applied Optics, 28, pp. 2297-2303, 1989.

Tearney et al., "Determination of the refractive index of highly scattering human tissue by optical coherence tomography", Optics Letters, 20(21), pp. 2258-2260, 1995.

Zysk et al., "Needle-based refractive index measurement using low-coherence interferometry", Optics Letters, 32, pp. 385-387, 2007.

Zysk et al., "Refractive index of carcinogen-induced rat mammary tumours", Phys. Med. Biol., 51, pp. 2165-2177, 2006.

Li et al., "Measurement method of the refractive index of biotissue by total internal reflection", Applied Optics, 35, pp. 1793-1795, 1996.

Knuttel et al., "Spatially confined and temporally resolved refractive index and scattering evaluation in human skin performed with optical coherence tomography", Journal of Biomedical Optics, 5, pp. 83-92, 2000.

Boppart et al., "Optical coherence tomography: feasibility for basic research and image-guided surgery of breast cancer", Breast Cancer Research and Treatment, vol. 84, pp. 85-97, 2004.

Liberman et al., "Palpable breast masses: Is there a role for percutaneous image-guided core biopsy?", American Journal of Roentgenology, vol. 175, pp. 779-787, 2000.

Bolivar et al., "Stereotaxic core needle aspiration biopsy with multiple passes in nonpalpable breast lesions", Acta Radiologica, vol. 39, pp. 389-394, 1998.

Acheson et al., "Histologic correlation of image-guided core biopsy with excisional biopsy of nonpalpable breast lesions", Archives of Surgery, vol. 132, pp. 815-821, 1997.

Pijnappel et al., "The diagnostic accuracy of core biopsy in palpable and non-palpable breast lesions", European Journal of Radiology, vol. 24, pp. 120-123, 1997.

Durduran et al., "Bulk optical properties of healthy female breast tissue", Physics in Medicine and Biology, vol. 47, pp. 2847-2861, 2002.

International Search Report dated Feb. 15, 2007 for International Application No. PCT/US2006/006618, 5 pages.

Marks et al., "Interferometric differentiation between resonant coherent anti-Stokes Raman scattering and nonresonant four-wave-mixing processes", Applied Physics Letters, vol. 85, No. 23, pp. 5787-5789, 2004.

Marks et al., "Nonlinear Interferometric Vibrational Imaging", Physical Review Letters, vol. 92, No. 12, pp. 123905-1-123905-4, 2004.

Boppart et al., "Contrast Enhancement Methods for Optical Coherence Tomography", Biophotonics/Optical Interconnects and VLSI Photonics/WBM Microactivities, 2004 Digest of the Leos Summer Topical Meetings, San Diego, CA, pp. 14-15, 2004.

Marks et al., "Pulse Shaping Strategies for Nonlinear Interferometric Vibrational Imaging Optimized for Biomolecular Imaging", Proceedings of the 26$^{th}$ Annual International Conference of the IEEE EMBS, San Francisco, CA, pp. 5300-5303, 2004.

Bredfeldt et al., "Nonlinear interferometric vibrational imaging of molecular species", Proc. Of SPIE, vol. 5321, pp. 149-156, 2004.

Easy Core Biopsy System, Product Brochure, Boston Scientific, 5 pages, 2004.

Yodh et al., "Spectroscopy and Imaging with Diffusing Light," Physics Today, pp. 34-40, 1995.

Roggan et al., in "Laser Induced Interstitial Thermotherapy", Muller, Ed., pp. 39-40,43, 1995.

Ohmi et al., "In Vitro Simultaneous Measurement of Refractive Index and Thickness of Biological Tissue by the Low Coherence Interferometry", IEEE Transactions on Biomedical Engineering, vol. 47, No. 9, pp. 1266-1270, 2000.

Luo et al., "Optical Biopsy of Lymph Node Morphology using Optical Coherence Tomography", Technology in Cancer Research & Treatment, vol. 4, No. 5, pp. 539-547, 2005.

Dehghani et al., "The effects of internal refractive index variation in near-infrared optical tomography: a finite element modelling approach", Physics in Medicine and Biology, 48, pp. 2713-2727, 2003.

Schmitt et al., "Turbulent nature of refractive-index variations in biological tissue", Optics Letters, vol. 21, No. 16, pp. 1310-1312, 1996.

Zysk et al., "Projected index computed tomography", Optics Letters, vol. 28, No. 9, pp. 701-703, 2003.

Easy Core Biopsy System, Product Brochure, Boston Scientific, 4 pages, 2004.

Evans et al., "Coherent anti-Stokes Raman scattering spectral interferometry: determination of the real and imaginary components of nonlinear susceptibility chi(3) for vibrational microscopy", Optics Letters, vol. 29, No. 24, pp. 2923-2925, 2004.

Yoon et al., "Dependence of line shapes in femtosecond broadband stimulated Raman spectroscopy on pump-probe timed delay", J Chem Phys., 122(2), p. 024505, 2005, 20 pages.

Kolomoitsev et al., "New problems of femtosecond time-domain CARS of large molecules", SPIE vol. 1402, pp. 31-43, 1990.

Mehendale et al, "Towards an anthrax detector using the femtosecond adaptive spectroscopic technique for coherent anti-Stokes Raman Spectroscopy: coherent anti-Stokes Raman spectroscopy signal from dipicolinic acid in bacterial spores", Journal of Modern Optics, vol. 51, pp. 2645-2653, 2004.

Invitation to pay additional fees and partial search report dated Apr. 4, 2008 for PCT application No. PCT/US2007/061364.

Huang, D. et al., "Optical Coherence Tomography", Science, 254, 5035, pp. 1178-1181, (1991).

Fercher, A.F. et al., "Optical Coherence Tomography—principles and applications", Institute of Physics Publishing, Reports on Progress in Physics, 66, pp. 239-303, (2003).

Boppart, S.A. et al., "Optical probes and techniques for molecular contrast enhancement in coherence imaging", J. Biomedical Optics, 10(4), pp. 041208-1 thru 041208-14, (2005).

Oldenburg, A.L. et al., "Imaging magnetically labeled cells with magnetomotive optical coherence tomography", Optics Letters, 30, 7, pp. 747-749, (2005).

Oldenburg, A.L. et al., "Selective OCT imaging of cells using magnetically-modulated optical contrast agents", in Proceedings of the Conference on Lasers and Electro-Optics, pp. 405-4-6, (2003).

Kopelman, R. et al., "Multifunctional nanoparticle platforms for in vivo MRI enhancement and photodynamic therapy of a rat brain cancer", J. Magnetism and Magnetic Materials, 293, pp. 404-410, (2005).

Romanus, E. et al., "Magnetic nanoparticle relaxation measurement as a novel tool for in vivo diagnostics", J. Magnetism and Magnetic Materials, 252, pp. 387-389, (2002).

Oldenburg, A.L. et al., "Magnetomotive contrast for in vivo optical coherence tomography", Optics Express, 13, 17, pp. 6597-6614, (2005).

Oh, J. et al., "Detection of magnetic nanoparticles in tissue using magneto-motive ultrasound", Nanotechnology, 17, pp. 4183-4190, (2006).

Joo, C. et al., "Spectral-domain optical coherence phase microscopy for quantitative phase-contrast imaging", Optics Letters, 30, 16, pp. 2131-2133, (2005).

Choma, M.A. et al., "Spectral-domain phase microscopy", Optics Letters, 30, 10, pp. 1162-1164, (2005).

Choma, M.A. et al. "Doppler flow imaging of cytoplasmic streaming using spectral domain phase microscopy", J. Biomedical Optics 11(2), pp. 024014-1 thru 024014-8, (2006).

Sticker, M. et al., "En face imaging of single cell layers by differential phase-contrast optical coherence microscopy", Optics Letters, 27, 13, pp. 1126-1128, (2002).

Sarunic, M.V. et al., "Full-field swept-source phase microscopy", Optics Letters, 31, 10, pp. 1462-1464, (2006).

De la Torre-Ibarra, M.H. et al., "Double-shot depth-resolved displacement field measurement using phase-contrast spectral optical coherence tomography", Optics Express, 14, 21, pp. 9643-9656, (2006).

Vakoc, B.J. et al., "Phase-resolved optical frequency domain imaging", Optics Express, 13, 14, pp. 5483-5493, (2005).

Pedersen, C.J. et al., "Phase-referenced Doppler optical coherence tomography in scattering media", Optics Letters, 30, 16, pp. 2125-2127, (2005).

Ren, H. et al., "Imaging and quantifying transverse flow velocity with the Doppler bandwidth in a phase-resolved functional optical coherence tomography", Optics Letters, 27, 6, pp. 409-411, (2002).

Zhao, Y. et al., "Doppler standard deviation imaging for clinical monitoring of in vivo human skin blood flow", Optics Letters, 25, 18, pp. 1358-1360, (2000).

Ren, H. et al., "Phase-resolved functional optical coherence tomography: simultaneous imaging of in situ tissue structure, blood flow velocity, standard deviation, birefringence, and Stokes vectors in human skin", Optics Letters, 27, 19, pp. 1702-1704, (2002).

Ding, Z. et al., "Real-time phase-resolved optical coherence tomography and optical Doppler tomography", Optics Express, 10, 5, pp. 236-244, (2002).

White, B.R. et al., "In vivo dynamic human retinal blood flow imaging using ultra-high-speed spectral domain optical Doppler tomography", Optics Express, 11, 25, pp. 3490-3496, (2003).

Ren, H. et al., "Real-time in vivo blood-flow imaging by moving-scatterer-sensitive spectral-domain optical Doppler tomography", Optics Letters, 31, 7, pp. 927-929, (2006).

Fang-Yen, C. et al., "Noncontact measurement of nerve displacement during action potential with a dual-beam low-coherence interferometer", Optics Letters, 29, 17, pp. 2028-2030, (2004).

Choma, M.A. et al., "Sensitivity advantage of swept source and Fourier domain optical coherence tomography", Optics Express, vol. 11, No. 18, pp. 2183-2189, (2003).

Leitgeb, R. et al., "Performance of *fourier domain* vs. *time domain* optical coherence tomography", Optics Express, 11, 8, pp. 889-894, (2003).

Leitgeb, R.A. et al., "Ultrahigh resolution Fourier domain optical coherence tomography", Optics Express, 12, 10, pp. 2156-2165, (2004).

De Boer, J.F. et al., "Improved signal-to-noise ratio in spectral-domain compared with time-domain optical coherence tomography", Optics Letters, 28, 21, pp. 2067-2069, (2003).

Ralston, T.S. et al., "Phase Stability Technique for Inverse Scattering in Optical Coherence Tomography", International Symposium on Biomedical Imaging, pp. 578-581, (2006).

Yang, C. "Molecular contrast optical coherence tomography: A review", Photochemistry and Photobiology 81, pp. 215-237, (2005).

Kim, J. et al., "Hemoglobin contrast in magnetomotive optical Doppler tomography", Optics Letters, 31, 6, pp. 778-780, (2006).

Oh, J. et al., "Magneto-motive detection of tissue-based macrophages by differential phase optical coherence tomography", Lasers in Surgery and Medicine, 39, pp. 266-272, (2007).

Crecea, V. et al., "Phase-resolved spectral-domain magnetomotive optical coherence tomography", Proc. of SPIE, 6429, pp. 64291X-1 thru 64291X-10, (2007).

Oldenburg, A.L. et al., "Magnetic contrast agents for optical coherence tomography", Proc. of SPIE, 5316, pp. 91-92, (2004).

Oldenburg, A.L. et al., "High-resolution in vivo nanoparticle imaigng using magnetomotive optical coherence tomography", Proc. of SPIE, 6097, pp. 609702-1 thru 609702-11, (2006).

Schmitt, J.M. "OCT elastography: imaging microscopic deformation and strain of tissue", Optics Express, 3, 6, pp. 199-211, (1998).

Gleich, B. et al., "Tomographic imaging using the nonlinear response of magnetic particles", Nature, 435, pp. 1214-1217, (2005).

Anker, J.N. et al., "Magnetically modulated optical nanoprobes", Applied Physics Letters, 82, 7, pp. 1102-1104, (2003).

Harisinghani, M.G. et al., "Noninvasive Detection of Clinically Occult Lymph-Node Metastases in Prostate Cancer", New England J. of Medicine, 348, 25, pp. 2491-2499, (2003).

Arbab, A.S. et al., "In vivo trafficking and targeted delivery of magnetically labeled stem cells", Human Gene Therapy, 15, pp. 351-360, (2004).

Alexiou, C. et al., "Locoregional cancer treatment with magnetic drug targeting", Cancer Research, 60, pp. 6641-6648, (2000).

Winter, P.M. et al., "Molecular imaging of angiogenesis in early-stage atherosclerosis with integrin-targeted nanoparticles", Circulation, 108, pp. 2270-2274, (2003).

Mornet S. et al., "Magnetic nanoparticle design for medical diagnosis and therapy", J. of Materials Chemistry, 14, pp. 2161-2175, (2004).

Kim, J. et al., "Imaging nanoparticle flow using magneto-motive optical Doppler tomography", Nanotechnology, 18, 035504, pp. 1-6, (2007).

Oldenburg, A.L. et al., "Spectral-Domain Magnetomotive OCT Imaging of Magnetic Nanoparticle Biodistribution", Proc. Of SPIE, vol. 6847, pp. 684719-1 thru 684719-8, (2008).

Oldenburg, A.L. et al., "Phase-resolved magnetomotive OCT for imaging nanomolar concentrations of magnetic nanoparticles in tissues", Optics Express, 16(15), pp. 11525-11539, (2008).

Oldenburg, A.L. et al., "Optical micro-scale mapping of dynamic biomechanical tissue properties", Optics Express, 16(15), pp. 11052-11065, (2008).

Oldenburg, A.L. et al., "Spectroscopic optical coherence tomography and microscopy", IEEE Journal of Selected Topics in Quantum Electronics, special issue on Biophotonics, 13(6), pp. 1629-1640, (2007).

Zysk, A.M. et al., "Optical coherence tomography: A review of clinical development from bench to bedside", Special section on optical diagnostic imaging from bench to bedside, Journal of Biomedical Optics, 12(5), pp. 051403-1 thru 051403-20, (2007).

Tan, W. et al., "Optical coherence tomography of cell dynamics in three-dimensional tissue models", Optics Express, 14(16), pp. 7159-7171, (2006).

Oldenburg, A.L. et al., "Plasmon-resonant gold nanorods as law backscattering albedo contrast agents for optical coherence tomography", Optics Express, vol. 14, No. 15, pp. 6724-6738, (2006).

Senin, A.A. et al., "Molecular dissociation observed with an atomic wavepacket and parametric four-wave mixing", Chemical Physics Letters, 381, pp. 53-59, (2003).

Oldenburg, A.L. et al., "Fast Fourier-domain delay line for in vivo optical coherence tomography with a polygonal scanner", Applied Optics, 42(22), pp. 4606-4611, (2003).

Marks, D.L. et al., "Autofocus algorithm for dispersion correction in optical coherence tomography", Applied Optics, 42(16), pp. 3038-3046, (2003).

Marks, D.L. et al., "Digital algorithm for dispersion correction in optical coherence tomography for homogeneous and stratified media", Applied Optics, vol. 42, No. 2, pp. 204-217, (2003).

Oldenburg, A.L. et al., "Vibrational wave packets in the $B^1\pi_u$ and $D^1\Sigma_u^+$ states of $Cs_2$: Determination of improved $Cs_2$+(X) and $Cs_2$(B) spectroscopic constants", Journal of Chemical Physics, 113(24), pp. 11009-11018, (2000).

Oldenburg, A.L. et al., "Optically pinpointing magnetic nanoparticles within biological tissue", Optics & Photonics News, 17(12), p. 24, (2006).

Nguyen, F.T. et al., "Magnetic protein microspheres as dynamic contrast agents for magnetomotive optical coherence tomography", Proc. of SPIE, 6867, pp. 68670F-1 thru 68670F-11, (2008).

Oldenburg, A.L. et al., "Plasmon-resonant gold nanorods provide spectroscopic OCT contrast in excised human breast tumors", Proc. of SPIE, 6867, pp. 68670E-1 thru 68670E-10, (2008).

Oldenburg, A.L. et al., "Spectral-domain magnetomotive OCT imaging of magnetic nanoparticle biodistribution", Proc. of SPIE, 6847, pp. 684719-1 thru 684719-11, (2008).

Liang, X. et al., "Modeling and measurement of tissue elastic moduli using optical coherence elastography", Proc. of SPIE, 6858, pp. 685803-1 thru 685803-8, (2008).

Oldenburg, A.L. et al., "Backscattering albedo contrast in OCT using plasmon-resonant gold nanorods", Proc. of SPIE, 6429, pp. 64291Z-1 thru 6429Z-8, (2007).

Oldenburg, A.L. et al., "Characterization of plasmon-resonant gold nanorods as near-infrared optical contrast agents investigated using a double-integrating sphere system", Proc. of SPIE, 5703, pp. 50-60, (2005).

Oldenburg, A.L. et al., "Magnetic contrast agents for optical coherence tomography." Proc. of SPIE, 5316, pp. 91-98, (2004).

Oldenburg, A.L. et al., "Optical manipulation of silicon microparticles in biological environments", Proc. of SPIE, 4962, pp. 249-255, (2003).

Oldenburg, A.L., "Wavepacket dynamics and time-domain spectroscopy in atomic rubidium", Quantum Electronics and Laser Science Conference 1999, Technical Digest, Thursday Morning, pp. 176-177, (1999).

Swanson, E.A. et al., "In vivo retinal imaging by optical coherence tomography", Optics Letters, 18, 21, pp. 1864-1866, (1993).

American Academy of Pediatrics, Clinical Practice Guideline, "Otitis Media with Effusion", Pediatrics, 113, 5, pp. 1412-1429, (2004).

Pitris, C. et al., "High-resolution imaging of the middle ear with optical coherence tomography: A feasibility study," Arch Otolaryngol Head Neck Surg., 127, pp. 637-642, (2001).

Hall-Stoodley, L. et al., "Direct detection of bacterial biofilms on the middle-ear mucosa of children with chronic otitis media," JAMA, 296, 2, pp. 202-211, (2006).

Xi, C. et al., "High-resolution three-dimensional imaging of biofilm development using optical coherence tomography," J. Biomed. Opt., 11(3), pp. 034001-1 thru 034001-6, (2006).

Leitgeb, R. et al., "Performance of *Fourier domain* vs. *time domain* optical coherence tomography," Optics Express, 11, 8, 889-894, (2003).

Ralston, T.S. et al., "Interferometric synthetic aperture microscopy", Nature Physics, 3, pp. 129-134, (2007).

Ralston, T.S. et al., "Inverse Scattering for Optical Coherence Tomography", J. Opt. Soc. Am. A, 23, 5, pp. 1027-1037, (2006).

Sitter, D.N. et al., "Three-dimensional Imaging: a Space invariant Model for Space Variant Systems", Applied Optics, 29, 26, pp. 3789-3794, (1990).

Choma, M.A. et al., "Sensitivity advantage of swept source and Fourier domain optical coherence tomography", Optics Express, 11, 18, pp. 2183-2189, (2003).

Ralston, T.S. et al., "Phase Stability Technique for Inverse Scattering in Optical Coherence Tomography", Biomedical Imaging: Nano to Macro, 3rd IEEE International Symposium on Biomedical Imaging, pp. 578-581, (2006).

Costerton, J.W. et al., "Bacterial biofilms: a common cause of persistent infections", Science, 284, pp. 1318-1322, (1999).

Donlan, R.M., "Biofilms and device-associated infections", Emerging Infectious Diseases, 7, 2, pp. 277-281, (2001).

Donlan, R.M. "Biofilms: microbial life on surfaces", Emerging Infectious Diseases, 8, 9, pp. 881-890, (2002).
Fux, C.A. et al., "Survival strategies of infectious biofilms", Trends in Microbiology, 13, 1, pp. 34-40, (2005).
Takata, G.S. et al., "Evidence Assessment of the Accuracy of Methods of Diagnosing Middle Ear Effusion in Children With Otitis Media With Effusion", Pediatrics, 112, 6, pp. 1379-1387, (2003).
Reed, W.A. et al., "Gradient-index fiber-optic microprobes for minimally invasive in vivo low-coherence interferometry," Optics Letters, 27, 20, pp. 1794-1796, (2002).
Vinegoni, C. et al., "Integrated structural and functional optical imaging combining spectral-domain optical coherence and multiphoton microscopy", Applied Physics Letters, 88, pp. 053901-1 thru 053901-3, (2006).
Crecea, V., "Phase-resolved spectral-domain magnetomotive optical coherence tomography for microscopic analysis of biomechanical properties", Preliminary Examination, pp. 1-15, (2007).
Xu, C. et al., "Near-infrared dyes as contrast-enhancing agents for spectroscopic optical coherence tomography", Optics Letters, vol. 29, No. 14, pp. 1657-1649, (2004).
Nguyen, F.T. et al., "Portable Real-Time Optical Coherence Tomography System for Intraoperative Imaging and Staging of Breast Cancer", Proc. Of SPIE, vol. 6430, pp. 64300H-1 thru 64300H1-10, (2007).
Zysk, A.M. et al., "Needle-probe system for the measurement of tissue refractive index", Proc. Of SPIE, vol. 6430, pp. 64300O-1-64300O-8, (2007).
Pasquesi, J.J. et al., "Detection of ultrastructural changes in genetically-altered and exercised skeletal muscle using PS-OCT", Proc. Of SPIE, vol. 6079, pp. 607926-1-607926-7, (2006).
Xu, C. et al., "Spectroscopic spectral-domain optical coherence microscopy", Optics Letters, vol. 31, No. 8, pp. 1079-1081, (2006).
Jones, G.W. et al., "High-spectral-resolution coherent anti-stokes raman scattering with interferometrically detected broadband chirped pulses", Optics Letters, vol. 31, No. 10, pp. 1543-1545, (2006).
Boppart, S.A., "Advances in contrast enhancement for optical coherence tomography", Proceedings of the $28^{th}$ IEEE EMBS Annual International Conference New York City, USA, pp. 121-124, Aug. 30-Sep. 3, 2006.
Marks, D.L. et al., "High numerical aperture full-field optical coherence tomography with space-invariant resolution without scanning the focus", Proc. Of SPIE, vol. 6429, pp. 64291R1-64291R-9, (2007).
Luo, W. et al., "Three-dimensional optical coherence tomography of the embryonic murine cardiovascular system", Journal of Biomedical Optics, vol. 11(2), pp. 021014-1-021014-8, (2006).
Marks, D.L. et al., "Inverse scattering for frequency-scanned full-field optical coherence tomography", Journal of the Optical Society of America A, vol. 24, No. 4, pp. 1034-1041, (2007).
Ralston, T.S. et al., "Inverse scattering for high-resolution interferometric microscopy", Optics Letters, vol. 31, No. 24, pp. 3585-3587, (2006).
Ralston, T.S. et al., "Demonstration of inverse scattering in optical coherence tomography", Proc. Of SPIE, vol. 6079, pp. 60791T-1-60791T-9, (2006).
Marks, D.L. et al., "Inverse scattering for rotationally scanned optical coherence tomography", J. Opt. Soc. Am. A, vol. 23, No. 10, pp. 2433-2439, (2006).
Zysk, A.M. et al., "Needle-based reflection refractometry of scattering samples using coherence-gated detection", Optics Express, vol. 15, No. 8, pp. 4787-4794, (2007).
Pasquesi, J.J. et al., "In vivo detection of exercise-induced ultrastructural changes in genetically-altered murine skeletal muscle using polarization-sensitive optical coherence tomography", Optics Express, vol. 14, No. 4, pp. 1547-1556, (2006).
Ko, H.J. et al. "Optical coherence elastography of engineered and developing tissue", Tissue Engineering, vol. 12, No. 1, pp. 63-73, (2006).
Zhu, C. et al., "Use of a multiseparation fiber optic probe for the optical diagnosis of breast cancer", Journal of Biomedical Optics, vol. 10(2), p. 024032-1-024032-13, (2005).
Bigio, I.J. et al., "Diagnosis of breast cancer using elastic-scattering spectroscopy: preliminary clinical results", Journal of Biomedical Optics, vol. 5, No. 2, pp. 221-228, (2000).
Bitar, R.A. et al., "Biochemical analysis of human breast tissues using Fourier-transform Raman spectroscopy", Journal of Biomedical Optics, vol. 11(5), p. 054001-1-054001-8, (2006).
Demos, S.G. et al., "Investigation of near-infrared autofluorescence imaging for the detection of breast cancer", IEEE Journal of Selected Topics in Quantum Electronics, vol. 11, No. 4, pp. 791-798, (2005).
Demos, S.G. et al., "Advances in optical spectroscopy and imaging of breast lesions", Journal of Mammary Gland Biology and Neoplasia, vol. 11, pp. 165-181, (2006).
Fournier, L.S. et al., "In-vivo NIR autofluorescence imaging of rat mammary tumors", Optics Express, vol. 14, No. 15, pp. 6713-6723, (2006).
Frank, C.J. et al., "Characterization of human breast biopsy specimens with near-IR Raman-spectroscopy", Analytical Chemistry, vol. 66, No. 3, pp. 319-326, (1994).
Gupta, P.K. et al., "Breast cancer diagnosis using $N_2$ laser excited autofluorescence spectroscopy", Lasers in Surgery and Medicine, vol. 21, pp. 417-422, (1997).
Haka, A.S. et al., "Identifying microcalcifications in benign and malignant breast lesions by probing differences in their chemical composition using Raman spectroscopy", Cancer Research, vol. 62, pp. 5375-5380, (2002).
Haka, A.S. et al., "Diagnosing breast cancer by using Raman spectroscopy", Proceedings of the National Academy of Sciences of the United States of America, vol. 102, No. 35, pp. 12371-12376, (2005).
Haka, A.S. et al., "In vivo margin assessment during partial mastectomy breast surgery using Raman spectroscopy", Cancer Research, vol. 66, pp. 3317-3322, (2006).
Iftimia, N.V. et al', "A portable, low coherence interferometry based instrument for fine needle aspiration biopsy guidance", Review of Scientific Instruments, vol. 76, p. 064301-1-064301-6, (2005).
Lenkinski, R.E. et al., "Near-infrared fluorescence imaging of microcalcification in an animal model of breast cancer", Academic Radiology, vol. 10, pp. 1159-1164, (2003).
Manoharan, R. et al., "Raman spectroscopy and fluorescence photon migration for breast cancer diagnosis and imaging", Photochemistry and Photobiology, vol. 67(1), pp. 15-22, (1998).
Motz, J.T. et al., "Optical fiber probe for biomedical Raman spectroscopy", Applied Optics, vol. 43, No. 3, pp. 542-554, (2004).
Palmer, G.M. et al., "Diagnosis of breast cancer using optical spectroscopy", Medical Laser Application, vol. 18, pp. 233-248, (2003).
Palmer, G.M. et al., "Comparison of multiexcitation fluorescence and diffuse reflectance spectroscopy for the diagnosis of breast cancer", IEEE Transactions on Biomedical Engineering, vol. 50, No. 11, pp. 1233-1242, (2003).
Peters, V.G. et al., "Optical properties of normal and diseased human breast tissues in the visible and near infrared", Physics in Medicine and Biology, vol. 35, No. 9, pp. 1317-1334, (1990).
Redd, D.C.B. et al., "Raman spectroscopic characterization of human breast tissues: Implications for breast cancer diagnosis", Applied Spectroscopy, vol. 47, No. 6, pp. 787-791, (1993).
Shafer-Peltier, A.S. et al., "Raman microspectroscopic model of human breast tissue: implications for breast cancer diagnosis in vivo", Journal of Raman Spectroscopy, vol. 33, pp. 552-563, (2002).
Shah, N. et al., "Noninvasive functional optical spectroscopy of human breast tissue", Proceedings of the National Academy of Sciences of the United States of America, vol. 98, No. 8, pp. 4420-4425, (2001).
Shetty, G. et al., "Raman spectroscopy: elucidation of biochemical changes in carcinogenesis of oesophagus", British Journal of Cancer, vol. 94, pp. 1460-1464, (2006).
Yang, Y. et al., "Fundamental differences of excitation spectrum between malignant and benign breast tissues", Photochemistry and Photobiology, vol. 66(4), pp. 518-522, (1997).
Zysk, A.M. et al., "Optical coherence tomography: a review of clinical development from bench to bedside", J. Biomedical Optics, 12(5), pp. 051403-1 thru 051403-21, (2007).
Choi, J.H. et al., "Multimodal biomedical imaging with asymmetric single-walled carbon nanotube/iron oxide nanoparticle complexes", Nano Letters, vol. 7, No. 4, pp. 861-867, (2007).

Zysk, A.M. et al., Comment on "In vivo cancer diagnosis with optical spectroscopy and acoustically induced blood stasis using a murine Mca35 model", Medical Physics, vol. 34, Issue 3, p. 1130, (2007).

Boppart, M.D. et al., "$\alpha_7\beta_1$-Integrin regulates mechanotransduction and prevents skeletal muscle injury", American Journal of Physiology: Cell Physiology, vol. 290, Issue 6, pp. C1660-C1665, (2006).

Toublan, F.J-J. et al., "Tumor targeting by surface-modified protein microspheres", Journal of the American Chemical Society, vol. 128, Issue 11, pp. 3472-3473, (2006).

Vinegoni, C. et al., "Integrated structural and functional optical imaging combining spectral-domain optical coherence and multiphoton microscopy", Applied Physics Letters, vol. 88, Issue 5, pp. 053901-1 thru 053901-3, (2006).

Vinegoni, C. et al., "Multi-modality imaging of structure and function combining spectral-domain optical coherence and multiphoton microscopy", Proc. of SPIE, vol. 6079, pp. 60791D-1 thru 60791D-8, (2006).

Boppart, S.A. et al., "Real-time optical biopsy and analysis of breast cancer using clinical optical coherence tomography", Journal of Clinical Oncology, Abstract presentation from the 2007 ASCO Annual Meeting Proceedings Part 1, vol. 25, No. 18S, (2007).

American Cancer Society, "2007 Cancer facts & figures", 56 pages, (2007).

Boppart, S.A. et al., "Optical coherence tomography: feasibility for basic research and image-guided surgery of breast cancer", Breast Cancer Research and Treatment, vol. 84, pp. 85-97, (2004).

Berg, W.A. et al., "Diagnostic accuracy of mammography, clinical examination, US, and MR imaging in preoperative assessment of breast cancer", Radiology, vol. 233, pp. 830-849, (2004).

Kawasaki, M., et al., "Diagnostic accuracy of optical coherence tomography and integrated backscatter intravascular ultrasound images for tissue characterization of human coronary plaques", Journal of the American College of Cardiology, vol. 48, No. 1, pp. 81-88, (2006).

Oldenburg, A.L. et al., "Molecular OCT contrast enhancement and imaging", Optical Coherence Tomography: Technology and Applications, Ch. 24, (2008).

Oldenburg, A.L. et al., "Optical coherence tomography", McGraw-Hill Encyclopedia of Science & Technology, (2005).

Oldenburg, A.L et al., "Imaging gold nanorods in excised human breast carcinoma by spectroscopic optical coherence tomography", Journal of Materials Chemistry, (2009).

Mehendale et al, "Towards an anthrax detector using the femtosecond adaptive spectroscopic technique for coherent anti-Stokes Raman Spectroscopy: coherent anti-Stokes Raman spectroscopy signal from dipicolinic acid in bacterial spores", Journal of Modern Optics, vol. 51, pp. 2645-2653, 2004.

Invitation to pay additional fees and partial search report dated Apr. 4, 2008 for PCT application No. PCT/US2007/061364.

Huang, D. et al., "Optical Coherence Tomography", Science, 254, 5035, pp. 1178-1181, (1991).

Fercher, A.F. et al., "Optical Coherence Tomography—principles and applications", Institute of Physics Publishing, Reports on Progress in Physics, 66, pp. 239-303, (2003).

Boppart, S.A. et al., "Optical probes and techniques for molecular contrast enhancement in coherence imaging", J. Biomedical Optics, 10(4), pp. 041208-1 thru 041208-14, (2005).

Oldenburg, A.L. et al., "Imaging magnetically labeled cells with magnetomotive optical coherence tomography", Optics Letters, 30, 7, pp. 747-749, (2005).

Oldenburg, A.L. et al., "Selective OCT imaging of cells using magnetically-modulated optical contrast agents", in Proceedings of the Conference on Lasers and Electro-Optics, pp. 405-4-6, (2003).

Kopelman, R. et al., "Multifunctional nanoparticle platforms for in vivo MRI enhancement and photodynamic therapy of a rat brain cancer", J. Magnetism and Magnetic Materials, 293, pp. 404-410, (2005).

Romanus, E. et al., "Magnetic nanoparticle relaxation measurement as a novel tool for in vivo diagnostics", J. Magnetism and Magnetic Materials, 252, pp. 387-389, (2002).

Oldenburg, A.L. et al., "Magnetomotive contrast for in vivo optical coherence tomography", Optics Express, 13, 17, pp. 6597-6614, (2005).

Oh, J. et al., "Detection of magnetic nanoparticles in tissue using magneto-motive ultrasound", Nanotechnology, 17, pp. 4183-4190, (2006).

Joo, C. et al., "Spectral-domain optical coherence phase microscopy for quantitative phase-contrast imaging", Optics Letters, 30, 16, pp. 2131-2133, (2005).

Choma, M.A. et al., "Spectral-domain phase microscopy", Optics Letters, 30, 10, pp. 1162-1164, (2005).

Choma, M.A. et al., "Doppler flow imaging of cytoplasmic streaming using spectral domain phase microscopy", J. Biomedical Optics 11(2), pp. 024014-1 thru 024014-8, (2006).

Sticker, M. et al., "En face imaging of single cell layers by differential phase-contrast optical coherence microscopy", Optics Letters, 27, 13, pp. 1126-1128, (2002).

Sarunic, M.V. et al., "Full-field swept-source phase microscopy", Optics Letters, 31, 10, pp. 1462-1464, (2006).

De la Torre-Ibarra, M.H. et al., "Double-shot depth-resolved displacement field measurement using phase-contrast spectral optical coherence tomography", Optics Express, 14, 21, pp. 9643-9656, (2006).

Vakoc, B.J. et al., "Phase-resolved optical frequency domain imaging", Optics Express, 13, 14, pp. 5483-5493, (2005).

Pedersen, C.J. et al., "Phase-referenced Doppler optical coherence tomography in scattering media", Optics Letters, 30, 16, pp. 2125-2127, (2005).

Ren, H. et al., "Imaging and quantifying transverse flow velocity with the Doppler bandwidth in a phase-resolved functional optical coherence tomography", Optics Letters, 27, 6, pp. 409-411, (2002).

Zhao, Y. et al., "Doppler standard deviation imaging for clinical monitoring of in vivo human skin blood flow", Optics Letters, 25, 18, pp. 1358-1360, (2000).

Ren, H. et al., "Phase-resolved functional optical coherence tomography: simultaneous imaging of in situ tissue structure, blood flow velocity, standard deviation, birefringence, and Stokes vectors in human skin", Optics Letters, 27, 19, pp. 1702-1704, (2002).

Ding, Z. et al., "Real-time phase-resolved optical coherence tomography and optical Doppler tomography", Optics Express, 10, 5, pp. 236-244, (2002).

White, B.R. et al., "In vivo dynamic human retinal blood flow imaging using ultra-high-speed spectral domain optical Doppler tomography", Optics Express, 11, 25, pp. 3490-3496, (2003).

Ren, H. et al., "Real-time in vivo blood-flow imaging by moving-scatterer-sensitive spectral-domain optical Doppler tomography", Optics Letters, 31, 7, pp. 927-929, (2006).

Fang-Yen, C. et al., "Noncontact measurement of nerve displacement during action potential with a dual-beam low-coherence interferometer", Optics Letters, 29, 17, pp. 2028-2030, (2004).

Choma, M.A. et al., "Sensitivity advantage of swept source and Fourier domain optical coherence tomography", Optics Express, vol. 11, No. 18, pp. 2183-2189, (2003).

Leitgeb, R. et al., "Performance of *fourier domain* vs. *time domain* optical coherence tomography", Optics Express, 11, 8, pp. 889-894, (2003).

Leitgeb, R.A. et al., "Ultrahigh resolution Fourier domain optical coherence tomography", Optics Express, 12, 10, pp. 2156-2165, (2004).

De Boer, J.F. et al., "Improved signal-to-noise ratio in spectral-domain compared with time-domain optical coherence tomography", Optics Letters, 28, 21, pp. 2067-2069, (2003).

Ralston, T.S. et al., "Phase Stability Technique for Inverse Scattering in Optical Coherence Tomography", International Symposium on Biomedical Imaging, pp. 578-581, (2006).

Yang, C. "Molecular contrast optical coherence tomography: A review", Photochemistry and Photobiology 81, pp. 215-237, (2005).

Kim, J. et al., "Hemoglobin contrast in magnetomotive optical Doppler tomography", Optics Letters, 31, 6, pp. 778-780, (2006).

Oh, J. et al., "Magneto-motive detection of tissue-based macrophages by differential phase optical coherence tomography", Lasers in Surgery and Medicine, 39, pp. 266-272, (2007).

Crecea, V. et al., "Phase-resolved spectral-domain magnetomotive optical coherence tomography", Proc. of SPIE, 6429, pp. 64291X-1 thru 64291X-10, (2007).

Oldenburg, A.L. et al., "Magnetic contrast agents for optical coherence tomography", Proc. of SPIE, 5316, pp. 91-92, (2004).
Oldenburg, A.L. et al., "High-resolution in vivo nanoparticle imaigng using magnetomotive optical coherence tomography", Proc. of SPIE, 6097, pp. 609702-1 thru 609702-11, (2006).
Schmitt, J.M. "OCT elastography: imaging microscopic deformation and strain of tissue", Optics Express, 3, 6, pp. 199-211, (1998).
Gleich, B. et al., "Tomographic imaging using the nonlinear response of magnetic particles", Nature, 435, pp. 1214-1217, (2005).
Anker, J.N. et al., "Magnetically modulated optical nanoprobes", Applied Physics Letters, 82, 7, pp. 1102-1104, (2003).
Harisinghani, M.G. et al., "Noninvasive Detection of Clinically Occult Lymph-Node Metastases in Prostate Cancer", New England J. of Medicine, 348, 25, pp. 2491-2499, (2003).
Arbab, A.S. et al., "In vivo trafficking and targeted delivery of magnetically labeled stem cells", Human Gene Therapy, 15, pp. 351-360, (2004).
Alexiou, C. et al., "Locoregional cancer treatment with magnetic drug targeting", Cancer Research, 60, pp. 6641-6648, (2000).
Winter, P.M. et al., "Molecular imaging of angiogenesis in early-stage atherosclerosis with integrin-targeted nanoparticles", Circulation, 108, pp. 2270-2274, (2003).
Mornet S. et al., "Magnetic nanoparticle design for medical diagnosis and therapy", J. of Materials Chemistry, 14, pp. 2161-2175, (2004).
Kim, J. et al., "Imaging nanoparticle flow using magneto-motive optical Doppler tomography", Nanotechnology, 18, 035504, pp. 1-6, (2007).
Oldenburg, A.L. et al., "Spectral-Domain Magnetomotive OCT Imaging of Magnetic Nanoparticle Biodistribution", Proc. Of SPIE, vol. 6847, pp. 684719-1 thru 684719-8, (2008).
Oldenburg, A.L. et al., "Phase-resolved magnetomotive OCT for imaging nanomolar concentrations of magnetic nanoparticles in tissues", Optics Express, 16(15), pp. 11525-11539, (2008).
Oldenburg, A.L. et al., "Optical micro-scale mapping of dynamic biomechanical tissue properties", Optics Express, 16(15), pp. 11052-11065, (2008).
Oldenburg, A.L. et al., "Spectroscopic optical coherence tomography and microscopy", IEEE Journal of Selected Topics in Quantum Electronics, special issue on Biophotonics, 13(6), pp. 1629-1640, (2007).
Zysk, A.M. et al., "Optical coherence tomography: A review of clinical development from bench to bedside", Special section on optical diagnostic imaging from bench to bedside, Journal of Biomedical Optics, 12(5), pp. 051403-1 thru 051403-20, (2007).
Tan, W. et al., "Optical coherence tomography of cell dynamics in three-dimensional tissue models", Optics Express, 14(16), pp. 7159-7171, (2006).
Oldenburg, A.L. et al., "Plasmon-resonant gold nanorods as law backscattering albedo contrast agents for optical coherence tomography", Optics Express, vol. 14, No. 15, pp. 6724-6738, (2006).
Senin, A.A. et al., "Molecular dissociation observed with an atomic wavepacket and parametric four-wave mixing", Chemical Physics Letters, 381, pp. 53-59, (2003).
Oldenburg, A.L. et al., "Fast Fourier-domain delay line for in vivo optical coherence tomography with a polygonal scanner", Applied Optics, 42(22), pp. 4606-4611, (2003).
Marks, D.L. et al., "Autofocus algorithm for dispersion correction in optical coherence tomography", Applied Optics, 42(16), pp. 3038-3046, (2003).
Marks, D.L. et al., "Digital algorithm for dispersion correction in optical coherence tomography for homogeneous and stratified media", Applied Optics, vol. 42, No. 2, pp. 204-217, (2003).
Oldenburg, A.L. et al., "Vibrational wave packets in the $B^1 \pi_u$ and $D^1\Sigma_u^+$ states of $Cs_2$: Determination of improved $Cs_2$+(X) and $Cs_2$(B) spectroscopic constants", Journal of Chemical Physics, 113(24), pp. 11009-11018, (2000).
Oldenburg, A.L. et al., "Optically pinpointing magnetic nanoparticles within biological tissue", Optics & Photonics News, 17(12), p. 24, (2006).
Nguyen, F.T. et al., "Magnetic protein microspheres as dynamic contrast agents for magnetomotive optical coherence tomography", Proc. of SPIE, 6867, pp. 68670F-1 thru 68670F-11, (2008).

Oldenburg, A.L. et al., "Plasmon-resonant gold nanorods provide spectroscopic OCT contrast in excised human breast tumors", Proc. of SPIE, 6867, pp. 68670E-1 thru 68670E-10, (2008).
Oldenburg, A.L. et al., "Spectral-domain magnetomotive OCT imaging of magnetic nanoparticle biodistribution", Proc. of SPIE, 6847, pp. 684719-1 thru 684719-11, (2008).
Liang, X. et al., "Modeling and measurement of tissue elastic moduli using optical coherence elastography", Proc. of SPIE, 6858, pp. 685803-1 thru 685803-8, (2008).
Oldenburg, A.L. et al., "Backscattering albedo contrast in OCT using plasmon-resonant gold nanorods", Proc. of SPIE, 6429, pp. 64291Z-1 thru 6429Z-8, (2007).
Oldenburg, A.L. et al., "Characterization of plasmon-resonant gold nanorods as near-infrared optical contrast agents investigated using a double-integrating sphere system", Proc. of SPIE, 5703, pp. 50-60, (2005).
Oldenburg, A.L. et al., "Magnetic contrast agents for optical coherence tomography." Proc. of SPIE, 5316, pp. 91-98, (2004).
Oldenburg, A.L. et al., "Optical manipulation of silicon microparticles in biological environments", Proc. of SPIE, 4962, pp. 249-255, (2003).
Oldenburg, A.L., "Wavepacket dynamics and time-domain spectroscopy in atomic rubidium", Quantum Electronics and Laser Science Conference 1999, Technical Digest, Thursday Morning, pp. 176-177, (1999).
Swanson, E.A. et al., "In vivo retinal imaging by optical coherence tomography", Optics Letters, 18, 21, pp. 1864-1866, (1993).
American Academy of Pediatrics, Clinical Practice Guideline, "Otitis Media with Effusion", Pediatrics, 113, 5, pp. 1412-1429, (2004).
Pitris, C. et al., "High-resolution imaging of the middle ear with optical coherence tomography: A feasibility study," Arch Otolaryngol Head Neck Surg., 127, pp. 637-642, (2001).
Hall-Stoodley, L. et al., "Direct detection of bacterial biofilms on the middle-ear mucosa of children with chronic otitis media," JAMA, 296, 2, pp. 202-211, (2006).
Xi, C. et al., "High-resolution three-dimensional imaging of biofilm development using optical coherence tomography," J. Biomed. Opt., 11(3), pp. 034001-1 thru 034001-6, (2006).
Leitgeb, R. et al., "Performance of *Fourier domain* vs. *time domain* optical coherence tomography," Optics Express, 11, 8, 889-894, (2003).
Ralston, T.S. et al., "Interferometric synthetic aperture microscopy", Nature Physics, 3, pp. 129-134, (2007).
Ralston, T.S. et al., "Inverse Scattering for Optical Coherence Tomography", J. Opt. Soc. Am. A, 23, 5, pp. 1027-1037, (2006).
Sitter, D.N. et al., "Three-dimensional Imaging: a Space invariant Model for Space Variant Systems", Applied Optics, 29, 26, pp. 3789-3794, (1990).
Choma, M.A. et al., "Sensitivity advantage of swept source and Fourier domain optical coherence tomography", Optics Express, 11, 18, pp. 2183-2189, (2003).
Ralston, T.S. et al., "Phase Stability Technique for Inverse Scattering in Optical Coherence Tomography", Biomedical Imaging: Nano to Macro, 3rd IEEE International Symposium on Biomedical Imaging, pp. 578-581, (2006).
Costerton, J.W. et al., "Bacterial biofilms: a common cause of persistent infections", Science, 284, pp. 1318-1322, (1999).
Donlan, R.M., "Biofilms and device-associated infections", Emerging Infectious Diseases, 7, 2, pp. 277-281, (2001).
Donlan, R.M. "Biofilms: microbial life on surfaces", Emerging Infectious Diseases, 8, 9, pp. 881-890, (2002).
Fux, C.A. et al., "Survival strategies of infectious biofilms", Trends in Microbiology, 13, 1, pp. 34-40, (2005).
Takata, G.S. et al., "Evidence Assessment of the Accuracy of Methods of Diagnosing Middle Ear Effusion in Children With Otitis Media With Effusion", Pediatrics, 112, 6, pp. 1379-1387, (2003).
Reed, W.A. et al., "Gradient-index fiber-optic microprobes for minimally invasive in vivo low-coherence interferometry," Optics Letters, 27, 20, pp. 1794-1796, (2002).

Vinegoni, C. et al., "Integrated structural and functional optical imaging combining spectral-domain optical coherence and multiphoton microscopy", Applied Physics Letters, 88, pp. 053901-1 thru 053901-3, (2006).

Crecea, V., "Phase-resolved spectral-domain magnetomotive optical coherence tomography for microscopic analysis of biomechanical properties", Preliminary Examination, pp. 1-15, (2007).

Xu, C. et al., "Near-infrared dyes as contrast-enhancing agents for spectroscopic optical coherence tomography", Optics Letters, vol. 29, No. 14, pp. 1657-1649, (2004).

Nguyen, F.T. et al., "Portable Real-Time Optical Coherence Tomography System for Intraoperative Imaging and Staging of Breast Cancer", Proc. of SPIE, vol. 6430, pp. 64300H-1 thru 64300H1-10, (2007).

Zysk, A.M. et al., "Needle-probe system for the measurement of tissue refractive index", Proc. of SPIE, vol. 6430, pp. 64300O-1-64300O-8, (2007).

Pasquesi, J.J. et al., "Detection of ultrastructural changes in genetically-altered and exercised skeletal muscle using PS-OCT", Proc. of SPIE, vol. 6079, pp. 607926-1-607926-7, (2006).

Xu, C. et al., "Spectroscopic spectral-domain optical coherence microscopy", Optics Letters, vol. 31, No. 8, pp. 1079-1081, (2006).

Jones, G.W. et al., "High-spectral-resolution coherent anti-stokes raman scattering with interferometrically detected broadband chirped pulses", Optics Letters, vol. 31, No. 10, pp. 1543-1545, (2006).

Boppart, S.A., "Advances in contrast enhancement for optical coherence tomography", Proceedings of the 28$^{th}$ IEEE EMBS Annual International Conference New York City, USA, pp. 121-124, Aug. 30-Sep. 3, 2006.

Marks, D.L. et al., "High numerical aperture full-field optical coherence tomography with space-invariant resolution without scanning the focus", Proc. Of SPIE, vol. 6429, pp. 64291R1-64291R-9, (2007).

Luo, W. et al., "Three-dimensional optical coherence tomography of the embryonic murine cardiovascular system", Journal of Biomedical Optics, vol. 11(2), pp. 021014-1-021014-8, (2006).

Marks, D.L. et al., "Inverse scattering for frequency-scanned full-field optical coherence tomography", Journal of the Optical Society of America A, vol. 24, No. 4, pp. 1034-1041, (2007).

Ralston, T.S. et al., "Inverse scattering for high-resolution interferometric microscopy", Optics Letters, vol. 31, No. 24, pp. 3585-3587, (2006).

Ralston, T.S. et al., "Demonstration of inverse scattering in optical coherence tomography", Proc. Of SPIE, vol. 6079, pp. 60791T-1-60791T-9, (2006).

Marks, D.L. et al., "Inverse scattering for rotationally scanned optical coherence tomography", J. Opt. Soc. Am. A, vol. 23, No. 10, pp. 2433-2439, (2006).

Zysk, A.M. et al., "Needle-based reflection refractometry of scattering samples using coherence-gated detection", Optics Express, vol. 15, No. 8, pp. 4787-4794, (2007).

Pasquesi, J.J. et al., "In vivo detection of exercise-induced ultrastructural changes in genetically-altered murine skeletal muscle using polarization-sensitive optical coherence tomography", Optics Express, vol. 14, No. 4, pp. 1547-1556, (2006).

Ko, H.J. et al., "Optical coherence elastography of engineered and developing tissue", Tissue Engineering, vol. 12, No. 1, pp. 63-73, (2006).

Zhu, C. et al., "Use of a multiseparation fiber optic probe for the optical diagnosis of breast cancer", Journal of Biomedical Optics, vol. 10(2), p. 024032-1-024032-13, (2005).

Bigio, I.J. et al., "Diagnosis of breast cancer using elastic-scattering spectroscopy: preliminary clinical results", Journal of Biomedical Optics, vol. 5, No. 2, pp. 221-228, (2000).

Bitar, R.A. et al., "Biochemical analysis of human breast tissues using Fourier-transform Raman spectroscopy", Journal of Biomedical Optics, vol. 11(5), p. 054001-1-054001-8, (2006).

Demos, S.G. et al., "Investigation of near-infrared autofluorescence imaging for the detection of breast cancer", IEEE Journal of Selected Topics in Quantum Electronics, vol. 11, No. 4, pp. 791-798, (2005).

Demos, S.G. et al., "Advances in optical spectroscopy and imaging of breast lesions", Journal of Mammary Gland Biology and Neoplasia, vol. 11, pp. 165-181, (2006).

Fournier, L.S. et al., "In-vivo NIR autofluorescence imaging of rat mammary tumors", Optics Express, vol. 14, No. 15, pp. 6713-6723, (2006).

Frank, C.J. et al., "Characterization of human breast biopsy specimens with near-IR Raman-spectroscopy", Analytical Chemistry, vol. 66, No. 3, pp. 319-326, (1994).

Gupta, P.K. et al., "Breast cancer diagnosis using $N_2$ laser excited autofluorescence spectroscopy", Lasers in Surgery and Medicine, vol. 21, pp. 417-422, (1997).

Haka, A.S. et al., "Identifying microcalcifications in benign and malignant breast lesions by probing differences in their chemical composition using Raman spectroscopy", Cancer Research, vol. 62, pp. 5375-5380, (2002).

Haka, A.S. et al., "Diagnosing breast cancer by using Raman spectroscopy", Proceedings of the National Academy of Sciences of the United States of America, vol. 102, No. 35, pp. 12371-12376, (2005).

Haka, A.S. et al., "In vivo margin assessment during partial mastectomy breast surgery using Raman spectroscopy", Cancer Research, vol. 66, pp. 3317-3322, (2006).

Iftimia, N.V. et al., "A portable, low coherence interferometry based instrument for fine needle aspiration biopsy guidance", Review of Scientific Instruments, vol. 76, p. 064301-1-064301-6, (2005).

Lenkinski, R.E. et al., "Near-infrared fluorescence imaging of microcalcification in an animal model of breast cancer", Academic Radiology, vol. 10, pp. 1159-1164, (2003).

Manoharan, R. et al., "Raman spectroscopy and fluorescence photon migration for breast cancer diagnosis and imaging", Photochemistry and Photobiology, vol. 67(1), pp. 15-22, (1998).

Motz, J.T. et al., "Optical fiber probe for biomedical Raman spectroscopy", Applied Optics, vol. 43, No. 3, pp. 542-554, (2004).

Palmer, G.M. et al., "Diagnosis of breast cancer using optical spectroscopy", Medical Laser Application, vol. 18, pp. 233-248, (2003).

Palmer, G.M. et al., "Comparison of multiexcitation fluorescence and diffuse reflectance spectroscopy for the diagnosis of breast cancer", IEEE Transactions on Biomedical Engineering, vol. 50, No. 11, pp. 1233-1242, (2003).

Peters, V.G. et al., "Optical properties of normal and diseased human breast tissues in the visible and near infrared", Physics in Medicine and Biology, vol. 35, No. 9, pp. 1317-1334, (1990).

Redd, D.C.B. et al., "Raman spectroscopic characterization of human breast tissues: Implications for breast cancer diagnosis", Applied Spectroscopy, vol. 47, No. 6, pp. 787-791, (1993).

Shafer-Peltier, A.S. et al., "Raman microspectroscopic model of human breast tissue: implications for breast cancer diagnosis in vivo", Journal of Raman Spectroscopy, vol. 33, pp. 552-563, (2002).

Shah, N. et al., "Noninvasive functional optical spectroscopy of human breast tissue", Proceedings of the National Academy of Sciences of the United States of America, vol. 98, No. 8, pp. 4420-4425, (2001).

Shetty, G. et al., "Raman spectroscopy: elucidation of biochemical changes in carcinogenesis of oesophagus", British Journal of Cancer, vol. 94, pp. 1460-1464, (2006).

Yang, Y. et al., "Fundamental differences of excitation spectrum between malignant and benign breast tissues", Photochemistry and Photobiology, vol. 66(4), pp. 518-522, (1997).

Zysk, A.M. et al., "Optical coherence tomography: a review of clinical development from bench to bedside", J. Biomedical Optics, 12(5), pp. 051403-1 thru 051403-21, (2007).

Choi'J.H. et al., "Multimodal biomedical imaging with asymmetric single-walled carbon nanotube/iron oxide nanoparticle complexes", Nano Letters, vol. 7, No. 4, pp. 861-867, (2007).

Zysk, A.M. et al., Comment on "In vivo cancer diagnosis with optical spectroscopy and acoustically induced blood stasis using a murine Mca35 model", Medical Physics, vol. 34, Issue 3, p. 1130, (2007).

Boppart, M.D. et al., "$\alpha_7 \beta_1$-Integrin regulates mechanotransduction and prevents skeletal muscle injury", American Journal of Physiology: Cell Physiology, vol. 290, Issue 6, pp. C1660-C1665, (2006).

Toublan, F.J-J. et al., "Tumor targeting by surface-modified protein microspheres", Journal of the American Chemical Society, vol. 128, Issue 11, pp. 3472-3473, (2006).

Vinegoni, C. et al., "Integrated structural and functional optical imaging combining spectral-domain optical coherence and multiphoton microscopy", Applied Physics Letters, vol. 88, Issue 5, pp. 053901-1 thru 053901-3, (2006).

Vinegoni, C. et al., "Multi-modality imaging of structure and function combining spectral-domain optical coherence and multiphoton microscopy", Proc. of SPIE, vol. 6079, pp. 60791 D-1 thru 60791D-8, (2006).

Boppart, S.A. et al., "Real-time optical biopsy and analysis of breast cancer using clinical optical coherence tomography", Journal of Clinical Oncology, Abstract presentation from the 2007 ASCO Annual Meeting Proceedings Part 1, vol. 25, No. 18S, (2007).

American Cancer Society, "2007 Cancer facts & figures", 56 pages, (2007).

Boppart, S.A. et al., "Optical coherence tomography: feasibility for basic research and image-guided surgery of breast cancer", Breast Cancer Research and Treatment, vol. 84, pp. 85-97, (2004).

Berg, W.A. et al., "Diagnostic accuracy of mammography, clinical examination, US, and MR imaging in preoperative assessment of breast cancer", Radiology, vol. 233, pp. 830-849, (2004).

Kawasaki, M., et al., "Diagnostic accuracy of optical coherence tomography and integrated backscatter intravascular ultrasound images for tissue characterization of human coronary plaques", Journal of the American College of Cardiology, vol. 48, No. 1, pp. 81-88, (2006).

Oldenburg, A.L. et al., "Molecular OCT contrast enhancement and imaging", Optical Coherence Tomography: Technology and Applications, Ch. 24, (2008).

Oldenburg, A.L. et al., "Optical coherence tomography", McGraw-Hill Encyclopedia of Science & Technology, (2005).

Oldenburg, A.L et al., "Imaging gold nanorods in excised human breast carcinoma by spectroscopic optical coherence tomography", Journal of Materials Chemistry, (2009).

* cited by examiner

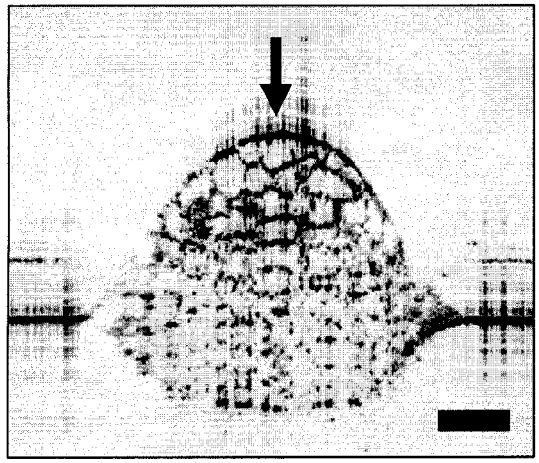 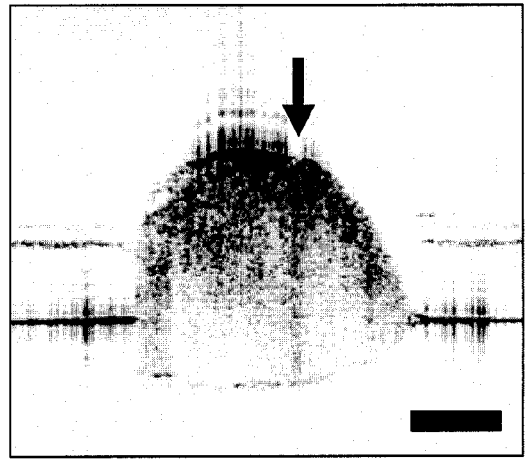
FIG. 12A                         FIG. 12B
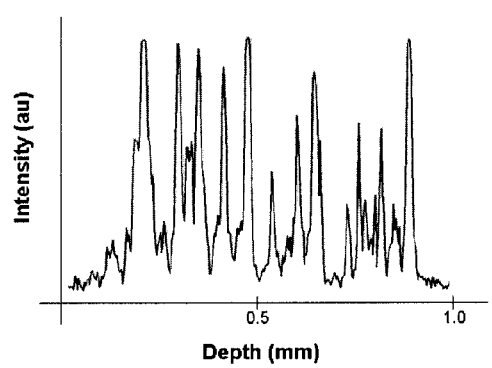 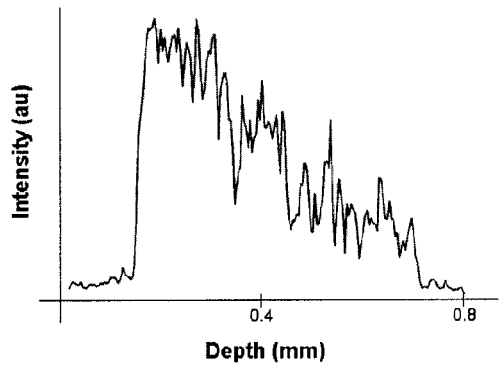
FIG. 13A                         FIG. 13B

METHOD AND APPARATUS FOR MEASUREMENT OF OPTICAL PROPERTIES IN TISSUE

REFERENCE TO RELATED APPLICATIONS

This application claims the benefit of U.S. Provisional Application No. 60/764,178 entitled "Method And Apparatus For Measurement Of Optical Properties In Tissue" filed Jan. 31, 2006, which is incorporated by reference in its entirety.

FEDERALLY SPONSORED RESEARCH OR DEVELOPMENT

The subject matter of this application may have been funded in part under a research grant from the National Institutes of Health, under NIH Grant Number 1 R01EB00108-1; and under a research grant from the National Science Foundation, under NSF East Asia Summer Institutes award number 0413596. The U.S. Government may have rights in this invention.

BACKGROUND

The removal of small samples of suspicious tissue by way of a biopsy is an important medical diagnostic procedure. The tissue samples that are removed may be subjected to full pathological testing in a laboratory to determine the presence and/or the degree of a medical disorder. A needle biopsy is a biopsy procedure in which a hollow needle is inserted into tissue to remove one or more tissue samples or to extract fluids of interest. Needle biopsies are typically performed to provide samples for diagnosis of breast cancer, prostate cancer, kidney disease, and liver disorders including cirrhosis, hepatitis, and liver cancer, among many others.

In the diagnosis and treatment of cancer, for example, tumor tissue may be obtained for detailed pathological analysis by fine needle aspiration biopsy or by core needle biopsy. If the tumor can be felt, the biopsy needle may be guided to the tumor tissue by palpation. For non-palpable tumors, the biopsy needle is typically guided by x-ray imaging (stereotaxis) or by ultrasound imaging (sonography). These conventional approaches to guiding biopsy needles, however, often yield tissue other than the tissue of interest, thereby leading to misdiagnosis or necessitating additional procedures.

Improvements in the accuracy of biopsy procedures would be beneficial, as the quality of the tissue samples analyzed can have significant effects on the accuracy of the diagnosis and the efficacy of the subsequent treatment. It would be desirable to provide a system for guiding a biopsy needle that could rapidly and accurately distinguish between different types of tissue. It would also be desirable to provide a system for guiding a biopsy needle that could distinguish between different pathologies.

SUMMARY

In one aspect, the invention provides a method of analyzing tissue including inserting a radiation source into tissue, impinging radiation upon the tissue, obtaining a sample signal of the radiation from the tissue, and determining a refractive index of the tissue from the sample signal. The method may further include determining at least one other optical property of the tissue.

In yet another aspect, the invention provides a method of identifying tissue including impinging radiation upon tissue, obtaining a sample signal of the radiation from the tissue, determining a refractive index of the tissue from the sample signal, and identifying the tissue by the refractive index. The method may further include identifying the tissue by the refractive index and at least one other optical property.

In yet another aspect, the invention provides a method of performing a biopsy of tissue including identifying tissue according to the above method, and biopsying at least a portion of the tissue. The method may further include repeating the identifying until a tissue of interest is identified, prior to biopsying at least a portion of the tissue.

In yet another aspect, the invention provides a probe including a housing, a radiation source, and a refractive index measurement assembly. The housing may include a distal end having a piercing tip. The probe may be attached to a guide needle and/or to a biopsy needle. This aspect may further include a probe where the radiation source includes an optical fiber having an exposed end, the refractive index measurement assembly includes a reflective surface and a gap between the exposed end and the reflective surface, and an optical path extends across the gap. This aspect may further include a probe where the refractive index measurement assembly includes an optical fiber having an exposed end and a gap between the radiation source and the exposed end, where an optical path extends across the gap. This aspect may further include a probe where the radiation source includes an optical fiber having an exposed end and an optical path extending from the exposed end, and the refractive index measurement assembly includes a radiation splitter and at least one lens, where the refractive index measurement assembly provides at least two foci separated along the optical path.

In yet another aspect, the invention provides a device for analyzing tissue including a low-coherence interferometer and a probe as described above, optically coupled to the interferometer.

In yet another aspect, the invention provides a computer readable medium including a computer program product having computer readable program code for determining a refractive index of tissue from a sample signal of radiation that has impinged upon the tissue. The determining the refractive index includes reading axial scan data from the sample signal, truncating the data to a range resulting from known tissue refractive index values, locating a maximum response intensity, calculating the refractive index using the maximum response intensity location, and outputting the resulting refractive index.

The following definitions are included to provide a clear and consistent understanding of the specification and claims.

The term "tissue" means an aggregate of cells and their intercellular substances.

The term "radiation" means electromagnetic radiation, including optical radiation in the visible, infrared, ultraviolet, or other spectral regions.

The term "sample signal" means at least a portion of the radiation that is scattered from, reflected from, and/or transmitted through a sample, including a tissue sample.

The term "optical property", with respect to tissue or other material, means a characteristic of the material that may be quantified by measuring a change in electromagnetic radiation when impinged upon the material, or an emission of radiation from the material.

The term "optical fiber" means an elongated fiber capable of transmitting radiation from one end to the other.

The term "optical path" means the path along which electromagnetic radiation propagates.

The term "pathlength" means the distance between two objects based on optical measurements. The pathlength through a medium between two objects is dependent on the refractive index of the medium, such that the pathlength may be different from the physical distance between the two objects.

The term "optically coupled" with respect to two components means that radiation may be transmitted from one component to the other component.

The term "distal", with respect to a probe or needle, means a position or direction that would be toward or inside the body of the patient when the probe or needle is inserted.

BRIEF DESCRIPTION OF THE DRAWINGS

The invention can be better understood with reference to the following drawings and description. The components in the figures are not necessarily to scale, emphasis instead being placed upon illustrating the principles of the invention.

FIG. 12A-B are optical coherence tomography (OCT) images from human breast tissue samples.

FIG. 13A-B are graphs of the axial intensity as a function of scan depth in the tissue, where the scan lines were along the arrows in FIGS. 12A and 12B, respectively.

DETAILED DESCRIPTION

The present invention makes use of the discovery that refractive index can be used to distinguish between different tissues, even if the tissues appear similar when examined by other imaging techniques. Mammalian tissues typically have a refractive index (n) near n=1.4, with variations ($\Delta n$) between cellular structures of up to approximately $\Delta n=0.07$. These variations may be used to distinguish between tissues that otherwise would require histological analysis. For example, the refractive indices of benign breast tumors and malignant breast tumors in humans have been reported as n=1.403 and n=1.431, respectively. Refractive index may be determined by interferometry with a sensitivity on the order of $\Delta n=0.007$ or less.

The present invention includes methods and apparatuses for analyzing and identifying tissue by determining refractive index, either alone or in combination with determining other optical properties of the tissue. The methods may be combined with biopsy procedures to improve the accuracy of the placement of the biopsy needle prior to removal of tissue. The apparatus may be used to identify tissue at a specific area in a patient, allowing a subsequently inserted biopsy needle to target the identified tissue for removal. The apparatus may also be combined with a biopsy needle in a single instrument.

Figure 1:
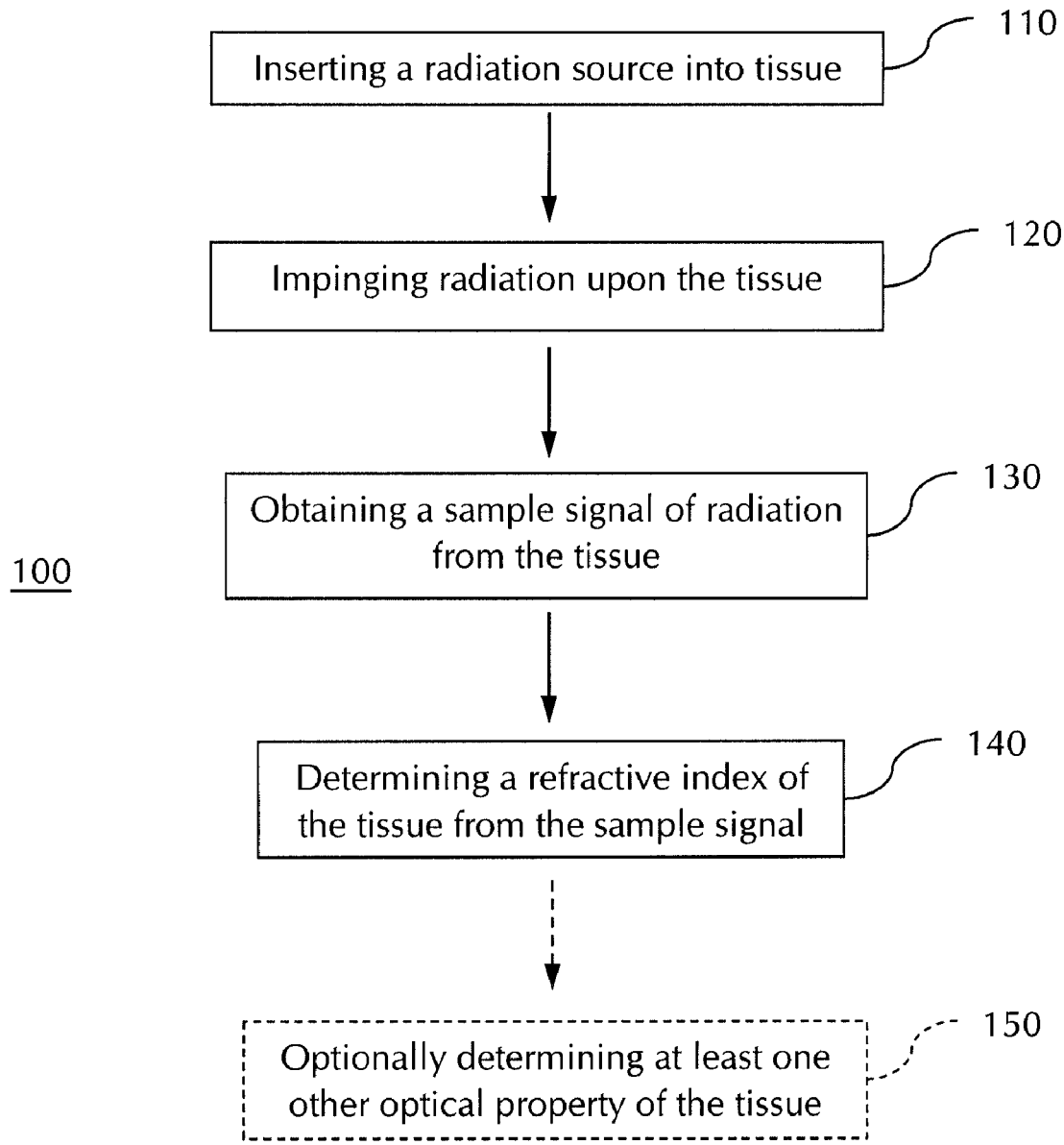
FIG. 1 depicts a method of analyzing tissue.

FIG. 1 represents a method 100 of analyzing tissue that includes inserting a radiation source into tissue 110, impinging radiation upon the tissue 120, obtaining a sample signal of the radiation from the tissue 130, and determining a refractive index of the tissue from the sample signal 140. The method 100 of analyzing tissue optionally includes determining at least one other optical property of the tissue 150.

Inserting a radiation source into tissue 110 may include inserting a probe into the tissue, where the probe includes a radiation source. Examples of radiation sources include, but are not limited to, optical fibers, light-emitting diodes (LEDs), and laser devices. Impinging radiation upon the tissue 120 may include emitting radiation from the radiation source to the tissue. The emitted radiation may pass through at least a portion of the tissue, or the radiation may be reflected from a surface of the tissue. In one example, a probe includes an optical fiber having an exposed end, and radiation may be passed to the tissue by passing radiation from one end of the optical fiber through the fiber and to the exposed end. The radiation emitted from the exposed end may then be transmitted along an optical path to the tissue. In another example, an LED in a probe may be connected to an electrical source sufficient to cause an emission of radiation to be transmitted along an optical path to the tissue.

Obtaining a sample signal of the radiation from the tissue 130 may include collecting radiation with an optical fiber. For example, radiation from the tissue may be collected by the same optical fiber from which the radiation was emitted, or it may be collected by a second optical fiber. Obtaining a sample signal 130 may include collecting radiation from the tissue with an electrooptic sensor. Examples of electrooptic sensors include, but are not limited to, charge-coupled devices (CCDs), photodiodes, photon multiplying tubes, or photoresistors.

Determining the refractive index of the tissue from the sample signal 140 may include combining the sample signal with a reference signal to produce an interferogram. The interferogram may be analyzed to determine the measured distance between two objects, and comparison of this measured distance with the physical distance between the objects may provide the refractive index of the portion of the tissue through which the radiation passes. Determining the refractive index 140 may include measuring the angle of displacement of the radiation as it passes through the tissue. For example, one or more electrooptic sensors may be located at a distance from the radiation source. The positions of the sensors detecting the maximum intensity of radiation from the tissue may then be correlated with the angle of refraction of the radiation through the tissue, from which the refractive index may be determined. Determining the refractive index of tissue from the sample signal 140 may include measuring the refractive index by reflection refractometry.

Optionally determining at least one other optical property of the tissue 150 may include determining one or more of the attenuation coefficient, the scattering profile, the anisotropy factor, the birefringence, the spectral shift, or the texture of the portion of the tissue through which the radiation passes. If the method is performed using interferometry, one or more of these optical properties may be determined from analysis of the interferogram.

The method 100 preferably is carried out using low-coherence interferometry. Low-coherence interferometry includes dividing low-coherence radiation between two paths in an interferometer, a reference path and a sample path. Radiation traveling along the reference path may be reflected off a reflective surface, as in a Michelson interferometer, or transmitted through an optical system or through free space, as in a Mach-Zender interferometer, prior to being collected as a reference signal. Radiation traveling along the sample path is transmitted to the tissue, and radiation that is scattered from, reflected from, and/or transmitted through the tissue may be collected as a sample signal. The sample and reference signals may be combined to form an interferogram, from which information about the properties of the tissue may be obtained. Direct measurement of the intensity of the interferogram using an electrooptic sensor may yield the response over a region of the tissue with a dimension in the propagation direction that is directly related to the coherence properties of the radiation source. The location of this tissue region is determined by the pathlength between the tissue region and the low-coherence radiation source, relative to the pathlength from the reference reflective surface to the low-coherence radiation source, since constructive interference is maximized for radiation passing over the same pathlength. The depth of the tissue response region may be changed by varying the reference path distance, thus changing the pathlength for which the maximum constructive interference occurs.

Figure 2:
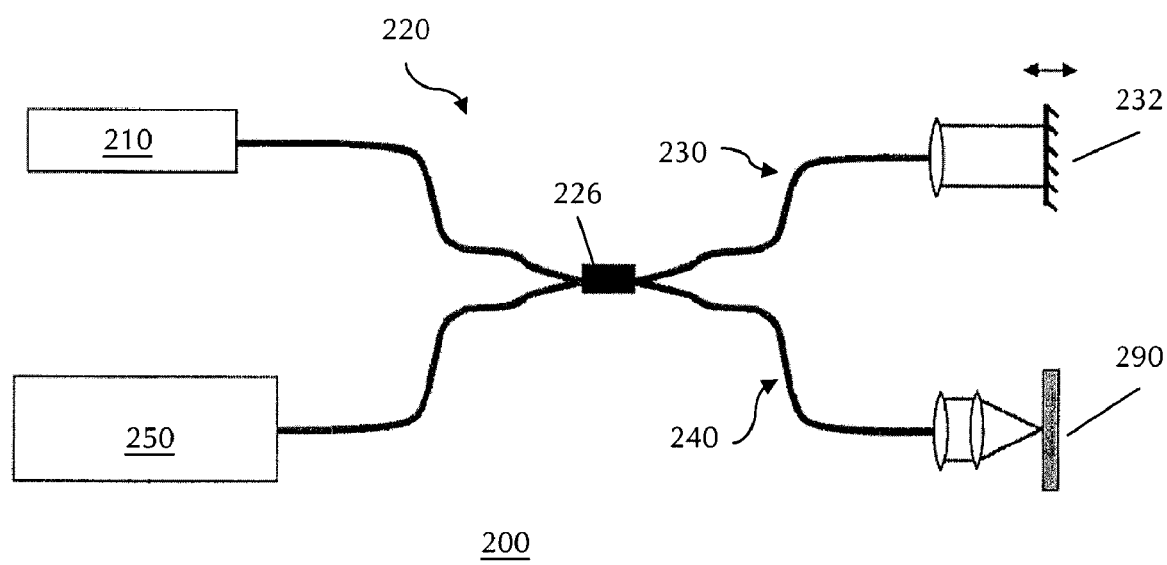
FIG. 2 is a schematic representation of a device for acquiring low-coherence interferometry data.

FIG. 2 is a schematic representation of a low-coherence interferometry device 200 for analyzing a portion of tissue 290. The device 200 includes a low-coherence laser source 210, a fiber optic assembly 220, a reference assembly 230, a sample assembly 240 and an analyzer 250. The fiber optic assembly 220 includes a beam splitter 226 that divides the radiation between the reference assembly 230 and the sample assembly 240. The reference assembly 230 includes a reference mirror 232, which may be moved toward or away from the fiber optic assembly 220. The sample assembly 240 exposes the tissue to the radiation and obtains a sample signal of the radiation that may be scattered, reflected and/or transmitted by the portion of the tissue that is exposed to the radiation. At least a portion of the sample assembly 240 of a low-coherence interferometry device may be incorporated into a probe that can be inserted into tissue in a patient. The radiation that is reflected from the reference assembly 230 constitutes the reference signal, and the reference signal and sample signal are combined to form an interferogram. The interferogram may be directed to the analyzer 250, or the reference and sample signals may be directed to the analyzer and then combined to form the interferogram. The analyzer 250 may process the signals to measure or display the low-coherence interferogram. The analyzer 250 may also determine the refractive index of the tissue and may optionally determine at least one other optical property of the tissue. The analyzer 250 may provide feedback, such as a visual display of the determined values of any optical properties and/or a signal indicating whether a particular tissue has been identified.

In one example of a low-coherence interferometry device, the low-coherence laser source is a Nd:YVO$_4$ pumped titanium: sapphire laser that yields radiation having a wavelength range from approximately 650 nm to approximately 900 nm after passing through a non-linear fiber. Dispersion and polarization are matched in the reference and sample assemblies. A precision galvanometer is used to scan a reference mirror, and non-linearities in galvanometer speed are relatively small so that interferometric triggering methods are not used. Special fibers, a 3-dB splitter, lenses, signal filtering, and demodulation are used to support the broad optical and electronic bandwidths. The analyzer collects the interferogram data at multiple reference mirror positions and digitizes the signal with an oversampling ratio of at least 2. For applications involving real time analysis, spectral detection with a CCD detector array or accelerated digitization and processing using a field-programmable gate array (FPCA) may be used.

Figure 3:
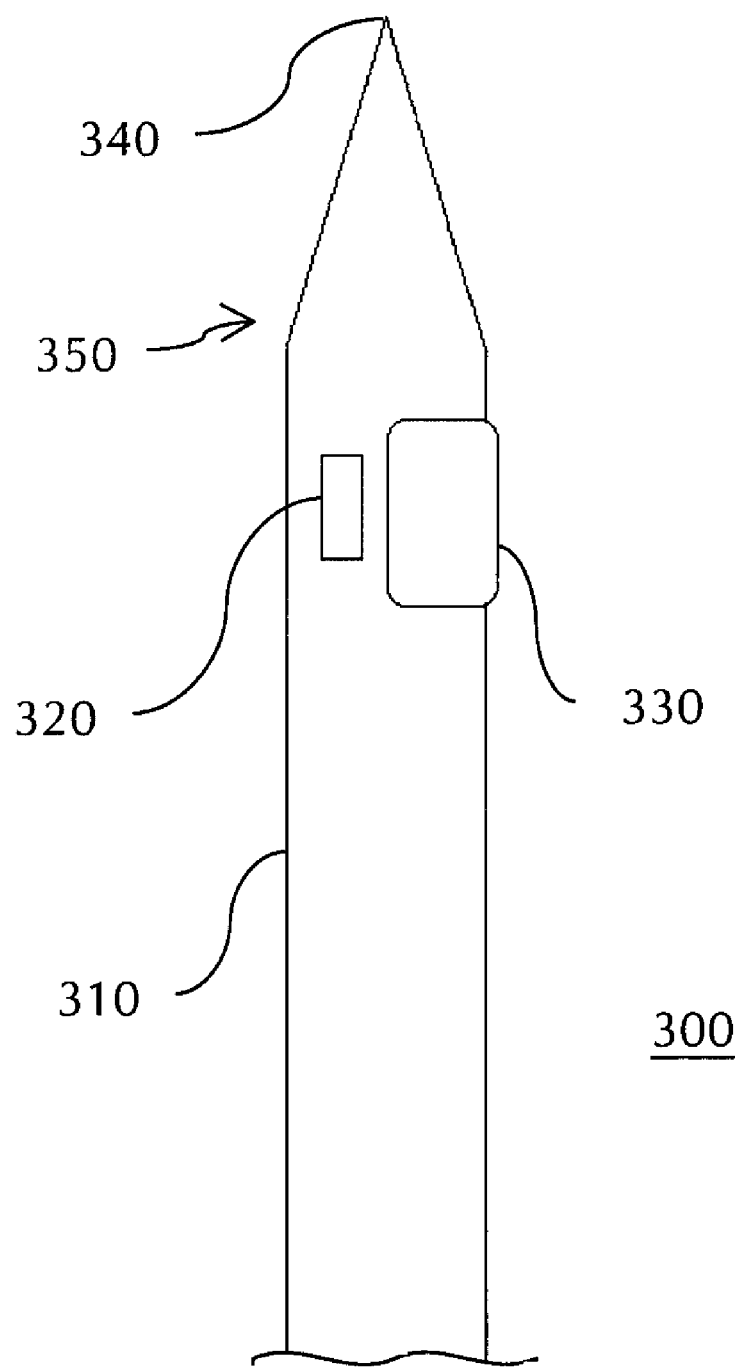
FIG. 3 is a cross-sectional representation of a probe containing a housing, a radiation source, and a refractive index measurement assembly.

FIG. 3 is a schematic representation of a probe 300 that includes a housing 310, a radiation source 320, and a refractive index measurement assembly 330. The housing 310 optionally may be configured as a needle with a piercing point 340 at the distal end 350 of the probe. In other configurations, the probe may be attached to a needle or to a medical device containing a needle. The width of the probe may be, for example, from 400 micrometers to 2.0 mm (27-14 gauge). Preferably the probe width is from 450 micrometers to 1.8 mm (26-15 gauge), and more preferably is from 500 to 900 micrometers (25-20 gauge). Preferably the probe size is minimized so as to reduce the invasiveness of the analysis procedure. The probe 300 may be optically coupled to a low-coherence interferometer device.

The radiation source 320 may include an optical fiber that introduces radiation from an external source. Radiation may be passed from one end of the optical fiber through the fiber and to the exposed end, so that the exposed end is a radiation source in the probe. The radiation emitted from the exposed end may then be transmitted along an optical path to the tissue. Typically, optical fibers are made of quartz, glass, or a transparent plastic, such as poly(methyl methacrylate) or polystyrene with a fluoropolymer cladding. Examples of optical fibers include single-mode fibers, multi-mode fibers, photonic-crystal fibers, hollow-core fibers, polarization-maintaining fibers and dual-clad fibers. Typical diameters for optical fibers are from 5 to 1,000 micrometers. The optical fiber may be a single-mode fiber or a multi-mode fiber. Single-mode glass fibers typically have diameters on the order of 10 micrometers. Multi-mode glass fibers typically have diameters on the order of 50-100 micrometers. Plastic optical fibers typically have diameters on the order of 1,000 micrometers.

The refractive index measurement assembly 330 may include one or more optical components configured to provide a measurement of the pathlength between two objects along an optical path traversed by the radiation. The refractive index of the tissue may be calculated by Equation 1:

$$n = L/d, \qquad \text{EQ. 1}$$

where n is the refractive index, L is the physical distance between two objects, and d is the measured pathlength between the two objects. The probe may also include one or more other devices for measuring the refractive index or other optical properties besides the refractive index.

One example of a refractive index measurement assembly includes a radiation splitter and one or more lenses configured to produce two foci separated along the optical path. The radiation splitter divides the incoming radiation into two distinguishable groups, providing for separate measurements of each focus point. Examples of radiation splitters include, but are not limited to, polarization modulators, beamsplitters, spectral filters, and cylindrical lenses. In this example, the L value is the distance between the foci when the probe is in air, and the d value is the measured distance between the foci when the probe is in the tissue.

Another example of a refractive index measurement assembly includes a reflective surface separated from an exposed end of an optical fiber at a known distance along the optical path. In this example, the L value is the physical distance between the exposed end of the optical fiber and the reflective surface, and the d value is the measured pathlength between the exposed end of the optical fiber and the reflective surface when the probe is in the tissue.

Another example of a refractive index measurement assembly includes an optical fiber having an exposed end, separated from the radiation source at a predetermined distance along the optical path, where the optical fiber is optically coupled to the low-coherence interferometer system. In this example, the L value is the physical distance between the radiation source and the exposed end of the optical fiber, and the d value is the measured pathlength between the radiation source and the exposed end of the optical fiber when the probe is in the tissue. The radiation source may be an optical fiber having an exposed end.

The refractive index measurement assembly 330 may include electrooptic sensors arranged to measure the angle of displacement of an optical path of the radiation as it passes through the sample. In this example, the refractive index of the tissue may be calculated by Equation 2:

$$n = n_{ref}(\sin \theta_{ref}/\sin \theta_{tissue}) \qquad \text{EQ. 2}$$

where n is the refractive index of the tissue, $n_{ref}$ is the refractive index of a reference medium, $\theta_{ref}$ is the angle between the incident radiation path and the measured radiation path in the reference medium, and $\theta_{tissue}$ is the angle between the incident radiation path and the measured radiation path in the tissue.

The probe 300 may include more than one refractive index measurement assembly. The probe 300 also may include a refractive index measurement assembly that includes two or more of the optical components described above. For example, a probe may include a radiation splitter and one or more lenses for measuring the distances between two foci, and also may include a reflective surface separated from the radiation source. In addition, the radiation source and the refractive index measurement assembly independently may include other optical or electrical components. For example, filters, prisms, gratings and lenses may be incorporated into one or more components of the probe.

In addition to refractive index, the probe 300 may facilitate the determination of one or more other optical properties of the portion of the tissue adjacent to the probe. For example, these other determinations may be arrived at by analysis of an interferogram from which the refractive index was determined. These other determinations may be arrived at by analysis of a different interferogram from which the refractive index was determined. For example, a different sample signal may be obtained by impinging low-coherence radiation upon a portion of the tissue and then collecting radiation from the portion of the tissue, where one or more of the optical components of the refractive index measurement assembly are bypassed. The use of a separate sample signal to determine other optical properties may yield increased accuracy of these determinations, since the sample signal parameters may be optimized separately for determination of the refractive index and for determination of the other optical properties.

One example of another optical property is the attenuation coefficient, which is a mathematical parameter governing the change in radiation intensity resulting from propagation through a medium. For a probe having a refractive index measurement assembly containing an object, such as a reflective surface or an optical fiber, at a fixed physical distance from the radiation source, the attenuation coefficient may be calculated by Equation 3:

$$\sigma = -\ln(I/I_o)/L, \qquad \text{EQ. 3}$$

where σ is the attenuation coefficient, I is the intensity of the radiation measured at the object in the tissue, $I_o$ is the intensity of the radiation at the object in a vacuum, and L is the is the physical distance between the object and the radiation source. The attenuation coefficient may also be calculated using an interferogram generated from radiation at another region within the tissue. See, for example, Faber, D. J. et al., "Quantitative measurement of attenuation coefficients of weakly scattering media using optical coherence tomography", *Optics Express*, 12(19), 4353-4365 (2004).

Another example of another optical property is the scattering profile, which is a measure of the intensity of radiation reflected or backscattered from the tissue as a function of depth within the tissue. This may be especially useful to identify boundaries between different types of tissues. The scattering profile is analogous to an optical coherence tomography (OCT) axial-scan, in which the tissue is scanned along the depth dimension (axially) as opposed to an OCT b-scan, which scans in two dimensions (both axially and laterally). See, for example, Fujimoto, J. G. et al., "Optical Coherence Tomography: An Emerging Technology for Biomedical Imaging and Optical Biopsy", *Neoplasia*, 2(1-2), 9-25 (2000). See also Zysk, A. M. et al., "Computational methods for analysis of human breast tumor tissue in optical coherence tomography images", *Journal of Biomedical Optics*, 11 (5), 054015-1 to 054015-7, 2006.

Another example of another optical property is the scattering coefficient, which is a mathematical parameter governing the change in radiation intensity due to scattering as a result of propagation through a medium. See, for example, Levitz, D. et al., "Determination of optical scattering properties of highly-scattering media in optical coherence tomography images", *Optics Express*, 12(2), 249-259 (2004).

Another example of another optical property is the anisotropy factor, which is a measure of the angle over which incoming radiation is scattered from a medium. See, for example, Levitz, D. et al., "Determination of optical scattering properties of highly-scattering media in optical coherence tomography images", *Optics Express*, 12(2), 249-259 (2004).

Another example of another optical property is the birefringence, which is a physical parameter governing the change in polarization of radiation due to propagation through a medium. See, for example, de Boer, J. F. et al., "Two-dimensional birefringence imaging in biological tissue by polarization-sensitive optical coherence tomography", *Optics Letters*, 25(2), 934-936 (1997).

Another example of another optical property is the spectral shift, which is a measure of the change in wavelength of the radiation due to propagation through a medium. See, for example, Morgner, U. et al., "Spectroscopic optical coherence tomography", *Optics Letters*, 25(2), 111-113 (2000).

Another example of another optical property is the texture, which is a measure of the local variations in brightness within a region of an image. See, for example, Gossage, K. W., "Texture analysis of optical coherence tomography images: feasibility for tissue classification", *Journal of Biomedical Optics*, 8(3), 570-575 (2003).

Further examples of optical properties that may be determined in addition to refractive index include Doppler shifts; phase resolution, including phase-resolved Doppler measurements and phase-resolved spectroscopic measurements; light scattering parameters; and spectroscopic absorption. The optical properties listed above may be used in a variety of combinations with refractive index measurements. The refractive index and one or more other optical properties may be determined continuously; or a single optical property determination may provide a baseline analysis, which is then augmented by the determination of the refractive index and/or one or more other optical properties.

Figure 4:
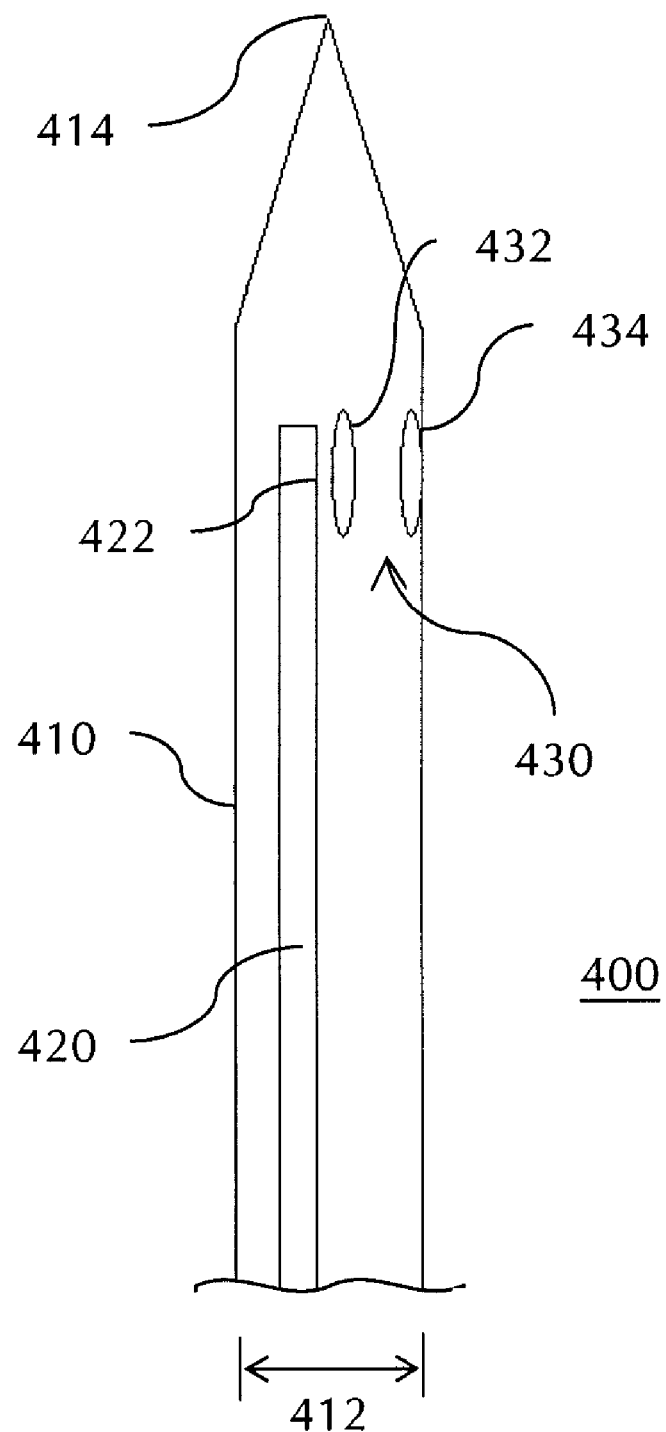
FIG. 4 is a cross-sectional representation of a probe containing a housing, an optical fiber and two lenses.

FIG. 4 is a cross-sectional representation of a probe 400 that includes a housing 410 having a width 412, an optical fiber 420 having an exposed end 422, and a refractive index measuring device 430 including a radiation splitter 432 and one or more lenses 434. Housing 410 has an optional piercing tip 414. The width 412 of housing 410 may be in the approximate range from 400 to 800 micrometers. Probe 400 may be inserted into tissue by piercing the tissue with optional piercing tip 414; by piercing the tissue with a needle connected to the probe; or by piercing the tissue with a needle, and then guiding the probe along the needle into the tissue. When the probe has been inserted into tissue, the exposed end 422 of the optical fiber 420 permits radiation that is passed through the optical fiber to travel along an optical path that includes a portion of the tissue that is adjacent the probe. The one or more lenses 434 produce two foci within the tissue, where the two foci are separated along the optical path. The probe 400 may be optically coupled to a low-coherence interferometer device.

Radiation that is reflected or backscattered from the tissue may be collected by the optical fiber 420 through exposed end 422. This collected radiation is a sample signal that may be combined with a reference signal to produce an interferogram. The pathlength between the two foci in the tissue as determined from the interferogram may be compared to the pathlength that would separate the foci in air by Equation 1 to provide the refractive index of the tissue. The pathlength that would separate the foci in air may be controlled by varying the parameters of the radiation splitter 432 and the one or more lenses 434. See, for example, Knüttel, A. et al., "Spatially confined and temporally resolved refractive index and scattering evaluation in human skin performed with optical coherence tomography", *Journal of Biomedical Optics*, 5(1), 83-92 (2000); and Zvyagin, A. V. et al., "Refractive index tomography of turbid media by bifocal optical coherence refractometry", *Optics Express*, 11(25), 3503-3517 (2003). Determining other optical properties of the portion of the tissue may include analyzing the interferogram used to determine the refractive index. Another sample signal may be obtained and combined with a reference signal to produce another interferogram, and this interferogram may be analyzed to determine one or more other optical properties.

Figure 5:
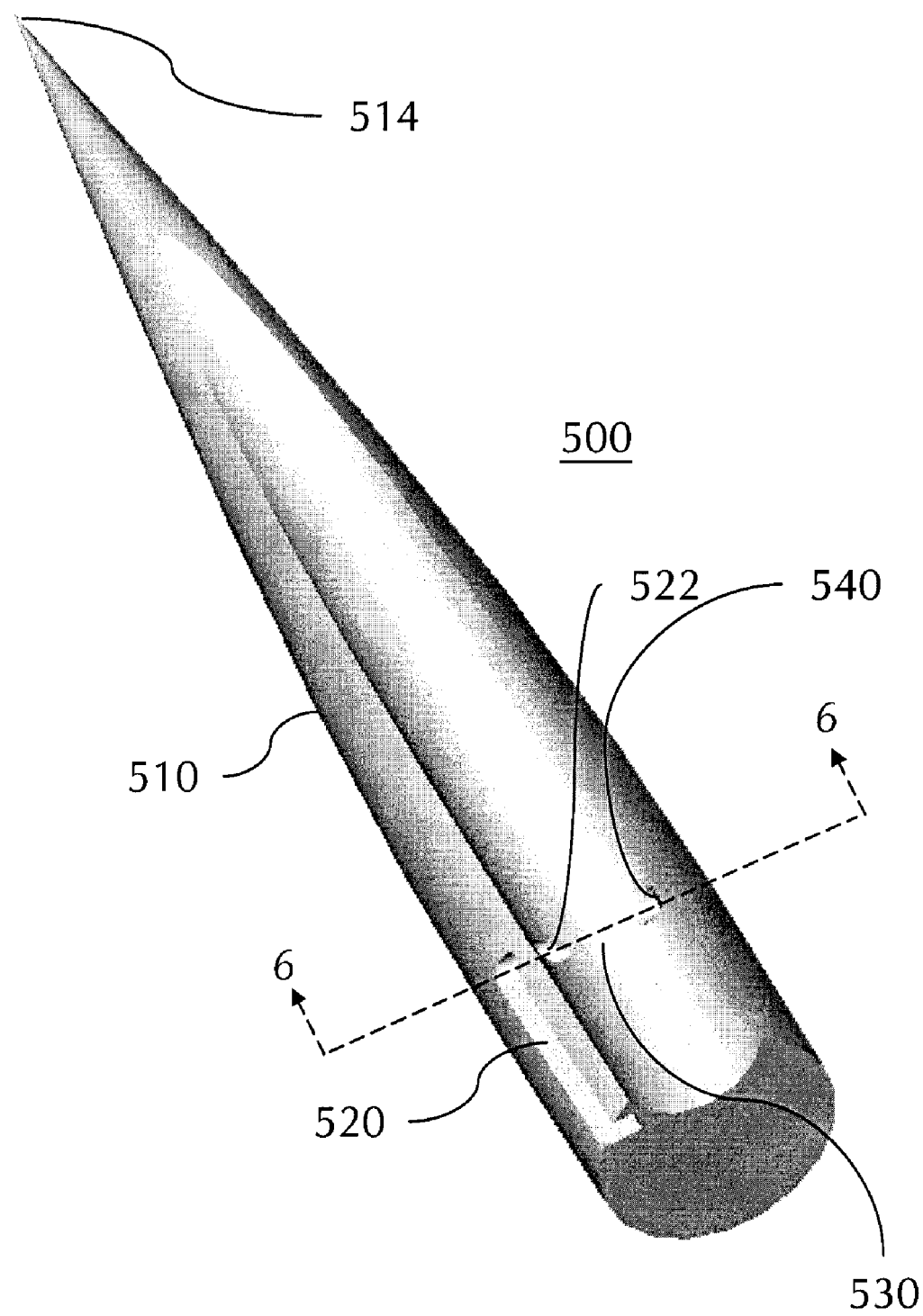
FIG. 5 is a perspective representation of a probe containing a housing, an optical fiber, a gap, and a reflective surface.
Figure 6:
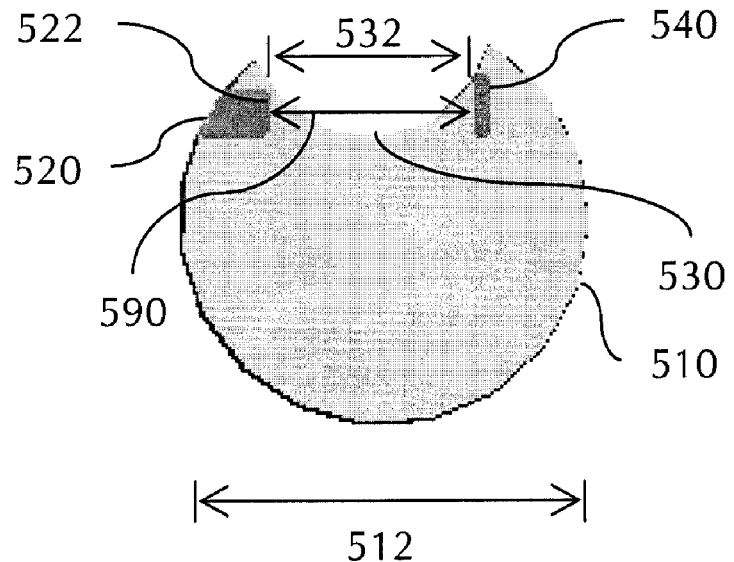
FIG. 6 is a cross-sectional representation along line 6-6 of the probe of FIG. 5.

FIG. 5 is a perspective view representation of a probe 500 that includes a housing 510, an optical fiber 520 having an exposed end 522, a gap 530, and a reflective surface 540. FIG. 6 is a cross-sectional representation of the probe 500, including the housing 510 having width 512, the optical fiber 520 having exposed end 522, the gap 530 having a distance 532, the reflective surface 540, and an optical path 590. Housing 510 has an optional piercing tip 514. The width 512 of housing 510 may be from 400 to 800 micrometers. The probe 500 may be optically coupled to a low-coherence interferometer device.

The exposed end 522 of the optical fiber 520 permits radiation that is passed through the optical fiber to travel along optical path 590, which traverses the distance 532 of the gap 530. When the probe has been inserted into tissue, the gap 530 may be filled with a portion of the tissue, such that the optical path 590 includes a portion of the tissue. The reflective surface 540 is positioned at the end of the optical path 590 and is separated from the exposed end 522 by the gap distance 532. Radiation that is transmitted through the portion of the tissue and reflected back by the reflective surface 540 may be collected by the optical fiber 520 through exposed end 522. This collected radiation is a sample signal that may be combined with a reference signal to produce an interferogram. Preferably the gap distance 532 is in the approximate range from 50 micrometers to 2.0 mm. More preferably the gap distance 532 is from 50 micrometers to 1.0 mm, more preferably is from 100 to 400 micrometers, and more preferably is from 120 to 200 micrometers. A focusing element, such as a GRIN lens, may be attached to the exposed end 522 of the optical fiber.

The optical pathlength from the exposed end 522 to the reflective surface 540 as determined from the interferogram may be compared to the physical gap distance 532 by Equation 1 to provide the refractive index of the tissue. Determining other optical properties of the tissue may include analyzing the interferogram used to measure the refractive index. Another sample signal may be obtained and combined with a reference signal to produce another interferogram, and this interferogram may be analyzed to determine one or more other optical properties.

Figure 8:
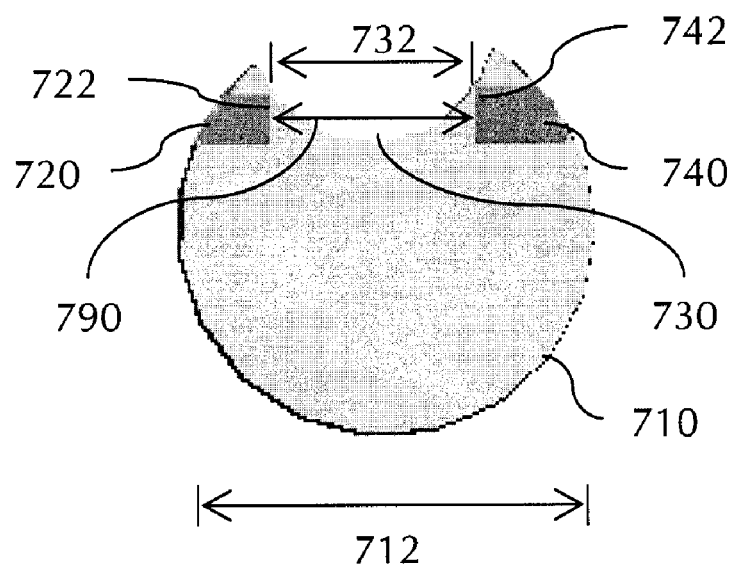
FIG. 8 is a cross-sectional representation along line 8-8 of the probe of FIG. 7.
Figure 7:
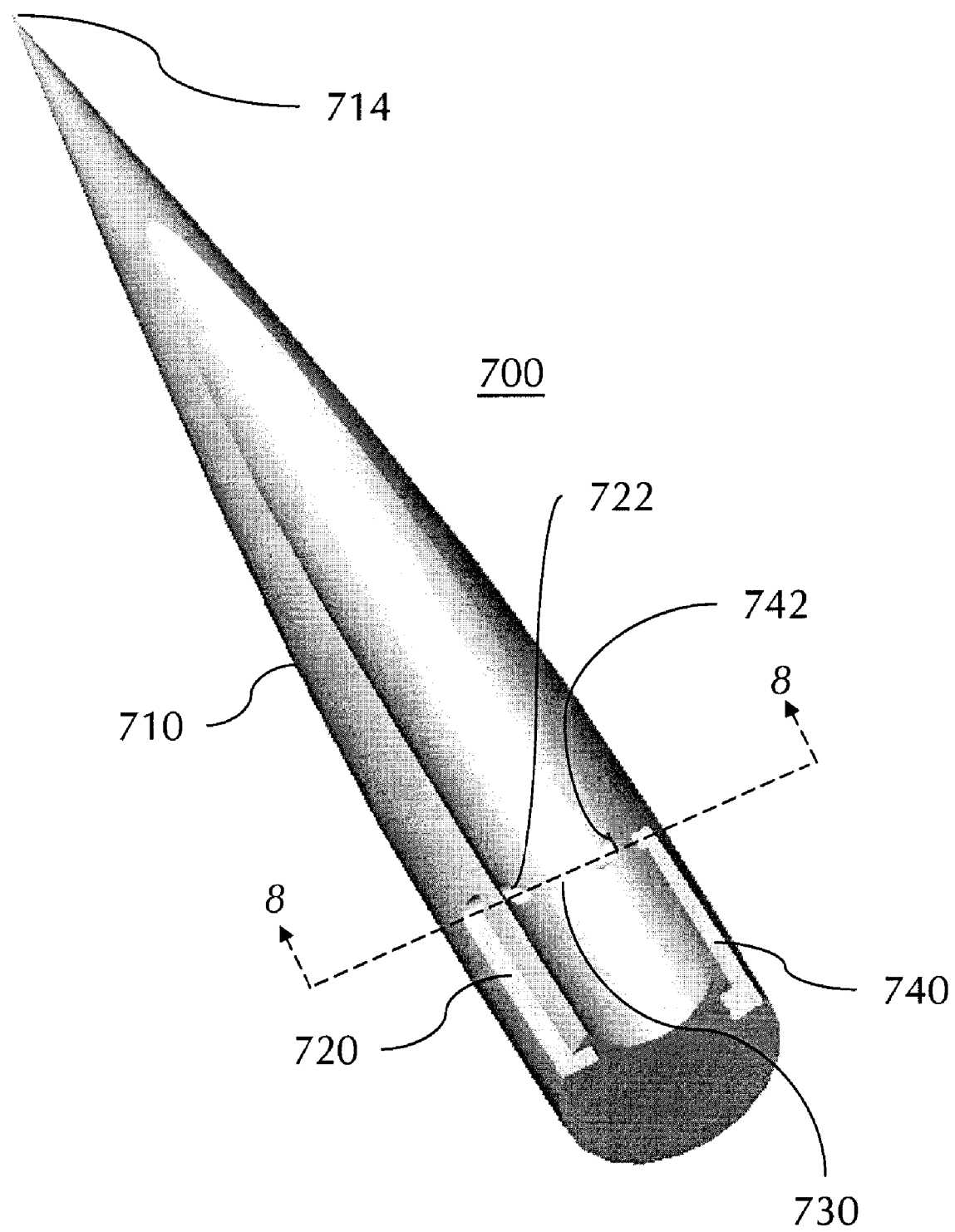
FIG. 7 is a perspective representation of a probe containing a housing, first and second optical fibers, and a gap.

FIG. 7 is a perspective view representation of a probe 700 that includes a housing 710, a first optical fiber 720 having a first exposed end 722, a gap 730, and a second optical fiber 740 having a second exposed end 742. FIG. 8 is a cross-sectional representation of the probe 700, including the housing 710 having width 712, the first optical fiber 720 having first exposed end 722, the gap 730 having a distance 732, the second optical fiber 740 having second exposed end 742, and an optical path 790. Housing 710 has an optional piercing tip 714. The width 712 of housing 710 may be in the approximate range from 400 to 800 micrometers. The probe 700 may be optically coupled to a low-coherence interferometer device.

The exposed end 722 of the optical fiber 720 permits radiation that is passed through the optical fiber to travel along optical path 790, which traverses the distance 732 of the gap 730. When the probe has been inserted into tissue, the gap 730 may be filled with a portion of the tissue, such that the optical path 790 lies within the portion of the tissue. The second exposed end 742 of the second optical fiber 740 is positioned at the end of the optical path 790 and is separated from the exposed end 722 by the gap distance 732. Preferably the gap distance 732 is in the approximate range from 50 micrometers to 2.0 mm. More preferably the gap distance 732 is from 50 micrometers to 1.0 mm, more preferably is from 100 to 400 micrometers, and more preferably is from 120 to 200 micrometers. Radiation that is transmitted through the portion of the tissue may be collected by the second optical fiber 740 through second exposed end 742. This collected radiation is a sample signal that may be combined with a reference signal to produce an interferogram. A focusing element, such as a GRIN lens, may be attached to the first exposed end 722 of the first optical fiber.

The optical pathlength from the exposed end 722 to the second exposed end 742 as determined from the interferogram may be compared to the gap distance 732 by Equation 1 to provide the refractive index of the tissue. Determining other optical properties of the tissue may include analyzing the interferogram used to determine the refractive index. Another sample signal may be obtained and combined with a reference signal to produce another interferogram, and this interferogram may be analyzed to determine one or more other optical properties. For example, radiation that is reflected or backscattered from the tissue sample may be collected by the first optical fiber 720 as a second sample signal. In this example, a first sample signal includes the transmitted radiation collected by second optical fiber 740, and a second sample signal includes the reflected or backscattered radiation collected by first optical fiber 720.

Figure 9:
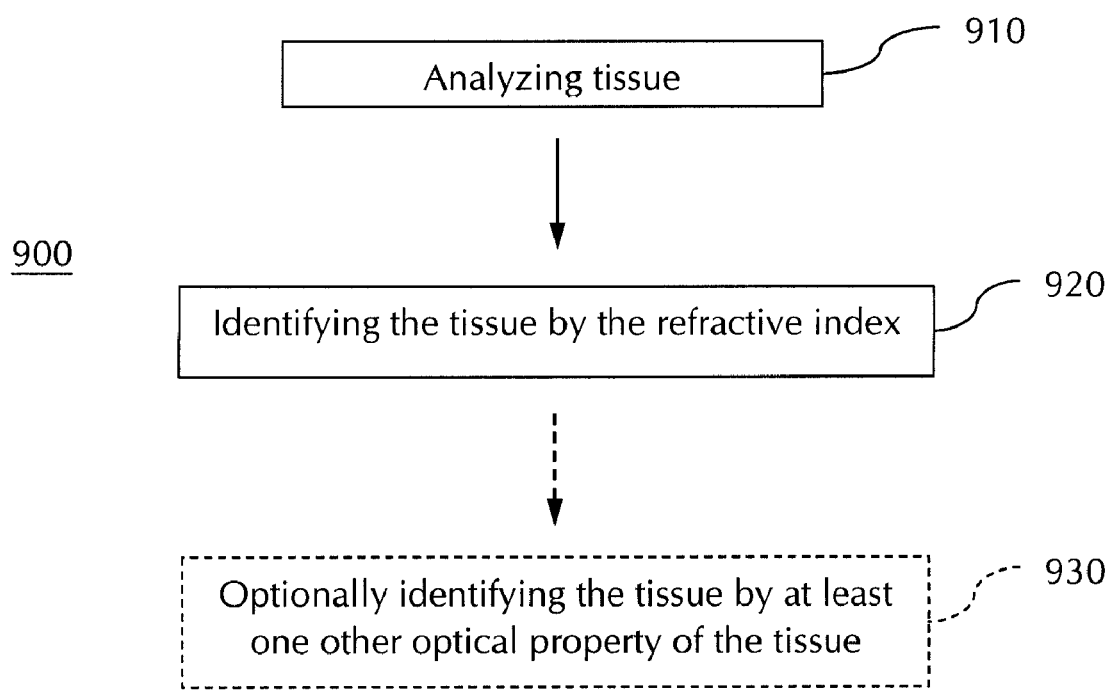
FIG. 9 depicts a method of identifying tissue.

FIG. 9 represents a method 900 of identifying tissue that includes analyzing tissue 910, identifying the tissue by the refractive index 920, and optionally identifying the tissue by at least one other optical property of the tissue 930. The method may be carried out in vivo, or it may be carried out ex vivo. The method 900 may be used to determine what type of tissue is present in a sample or in an organism and may further be used to determine the condition of that tissue. For example, the method may be used to determine whether the tissue is fat tissue, breast tissue or tumor tissue. In another example, the method may be used to determine whether tumor tissue is benign, malignant or metastatic.

Analyzing tissue 910 may include impinging radiation upon tissue, obtaining a sample signal of the radiation from the tissue, determining the refractive index of the tissue from the sample signal, and optionally determining at least one other optical property of the tissue. Analyzing tissue 910 may also include inserting a radiation source into tissue prior to impinging radiation upon the tissue. For example, a guide needle containing a probe may be inserted into the tissue, where the probe includes a housing, a radiation source and a refractive index measurement assembly on a guide needle.

Identifying the tissue by the refractive index 920 may include comparing the determined refractive index with known refractive indices of various tissues. Refractive index values of tissue are reported, for example, in Gottschalk, W., "Ein Meßverfahren zur Bestimmung der optischen Parameter biologisher Gwebe in vitro", *Dissertation* 93 HA 8984, Universität Fridericiana Karlsruhe, 1992; and in Bolin, F. P. et al., "Refractive index of some mammalian tissues using a fiber optic cladding method," *Applied Optics,* 28, 2297-2303 (1989).

Optionally identifying the tissue by at least one other optical property 930 may include comparing the determined optical property with known values of the optical property for various tissues. These comparisons may be done sequentially and in any order. For example, the comparison of refractive index may reduce the number of possible tissue types to only those types having a refractive index within a numerical margin around the determined refractive index. The second comparison may then be used to identify the tissue from this reduced set. These comparisons also may be done simultaneously. For example, the determined refractive index and at least one other determined optical property may be compared to the known combinations of these values to identify the tissue having the highest overall correlation to both values.

Figure 10:
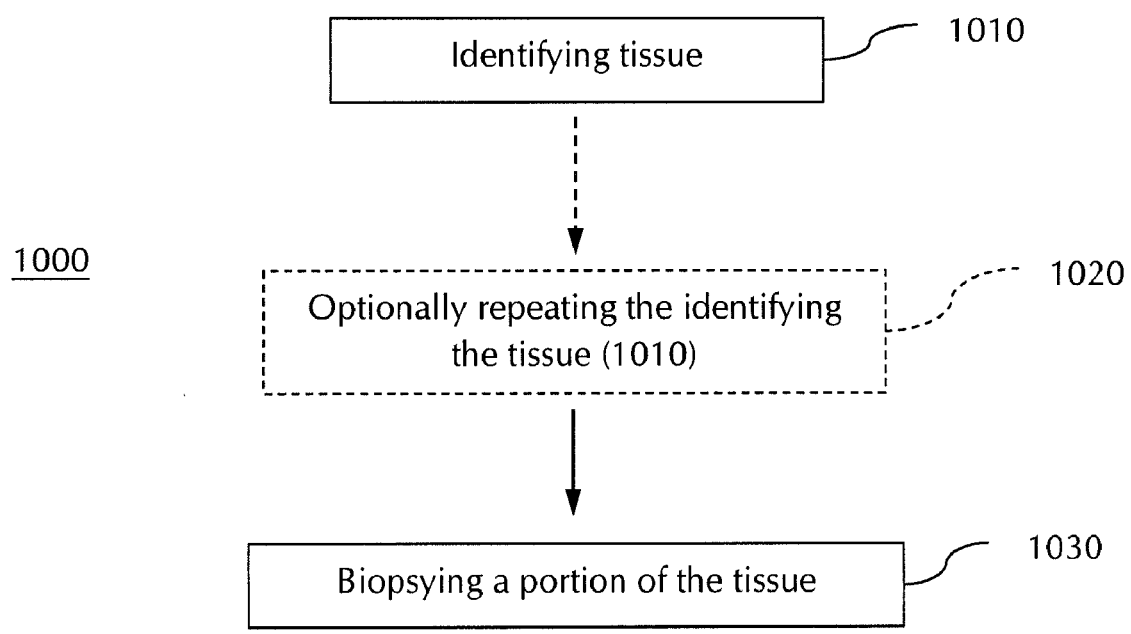
FIG. 10 depicts a method of performing a biopsy of a tissue of interest.

FIG. 10 represents a method 1000 of performing a biopsy of a tissue of interest that includes identifying tissue 1010, optionally repeating the identifying tissue 1020, and biopsying a portion of the tissue 1030. Identifying tissue 1010 may include inserting a radiation source into tissue, impinging radiation upon the tissue, obtaining a sample signal of the radiation from the tissue, determining the refractive index of the tissue from the sample signal, optionally determining at least one other optical property of the tissue, identifying the tissue by the refractive index, and optionally identifying the tissue by at least one other optical property of the tissue.

Identifying tissue 1010 may include inserting a guide needle containing a probe, where the probe includes a housing, a radiation source and a refractive index measurement assembly on a guide needle. After being used to identify the tissue of interest the probe may be removed from the tissue, leaving the guide needle in position at the tissue of interest, or the probe may be maintained in position with the guide needle. A biopsy needle may be inserted into the tissue by way of the guide needle, placed at the tissue of interest, and activated to biopsy a portion of the tissue 1030. Identifying tissue 1010 may also include inserting a biopsy needle containing a probe, where the probe includes a housing, a radiation source and a refractive index measurement assembly on a guide needle. In this way, a single apparatus may be used to guide the biopsy needle and to biopsy a portion of the tissue 1030.

Identifying tissue 1010 may further include determining whether the identified tissue matches the tissue of interest to be biopsied. This determination may be performed manually, or it may be performed automatically through a feedback system. In one example, a feedback system may include a visual and/or audio display of the refractive index of the tissue, and optionally of at least one other optical property of the tissue. In another example, a feedback system may include a visual and/or audio display of the type of tissue that has been identified. In another example, a feedback system may include a visual and/or audio signal indicating if a preselected tissue of interest has or has not been identified.

The optionally repeating the identifying 1020 may be performed if the identified tissue does not match the tissue of interest to be biopsied. The optional repeating may include moving a probe from one location to another location within the tissue. If the tissue at the new location still does not match the tissue of interest, the repeating may be performed again, and this process may be continued until the tissue of interest is identified.

Biopsying a portion of the tissue 1030 may be performed with a conventional biopsy needle, such as an Easy Core® core biopsy needle (Boston Scientific Corporation, Natick, Mass.), a Surecut™ aspiration biopsy needle (Boston Scientific), a Max Core® biopsy needle (Bard Biopsy Systems, Tempe, Ariz.), a Quick-Core® biopsy needle (Cook, Inc., Bloomington, Ind.), or a multi-hole aspiration biopsy needle (Millex Products, Inc., Chicago, Ill.). If the guide needle and probe are maintained in the tissue during the procedure, the biopsy needle may be removed, and the guide needle and probe may be repositioned until the tissue of interest is again identified or until another tissue of interest is identified. For example, the guide needle and probe may be repositioned to another tumor within the normal tissue. A biopsy needle may again be inserted along the guide needle, and another tissue sample may be biopsied.

Implementations of the tissue analysis methods, the tissue identification methods, and the tissue biopsy methods each may include computer readable program code. These algorithms, devices and systems may be implemented together or independently. Such code may be stored on a processor, a memory device or on any other computer readable storage medium. The program code may be encoded in a computer readable electronic or optical signal. The code may be object code or any other code describing or controlling the functionality described in this application. The computer readable storage medium may be a magnetic storage disk such as a floppy disk; an optical disk such as a CD-ROM; semiconductor memory or any other physical object storing program code or associated data. A computer readable medium may include a computer program product including the computer readable program code.

Figure 11:
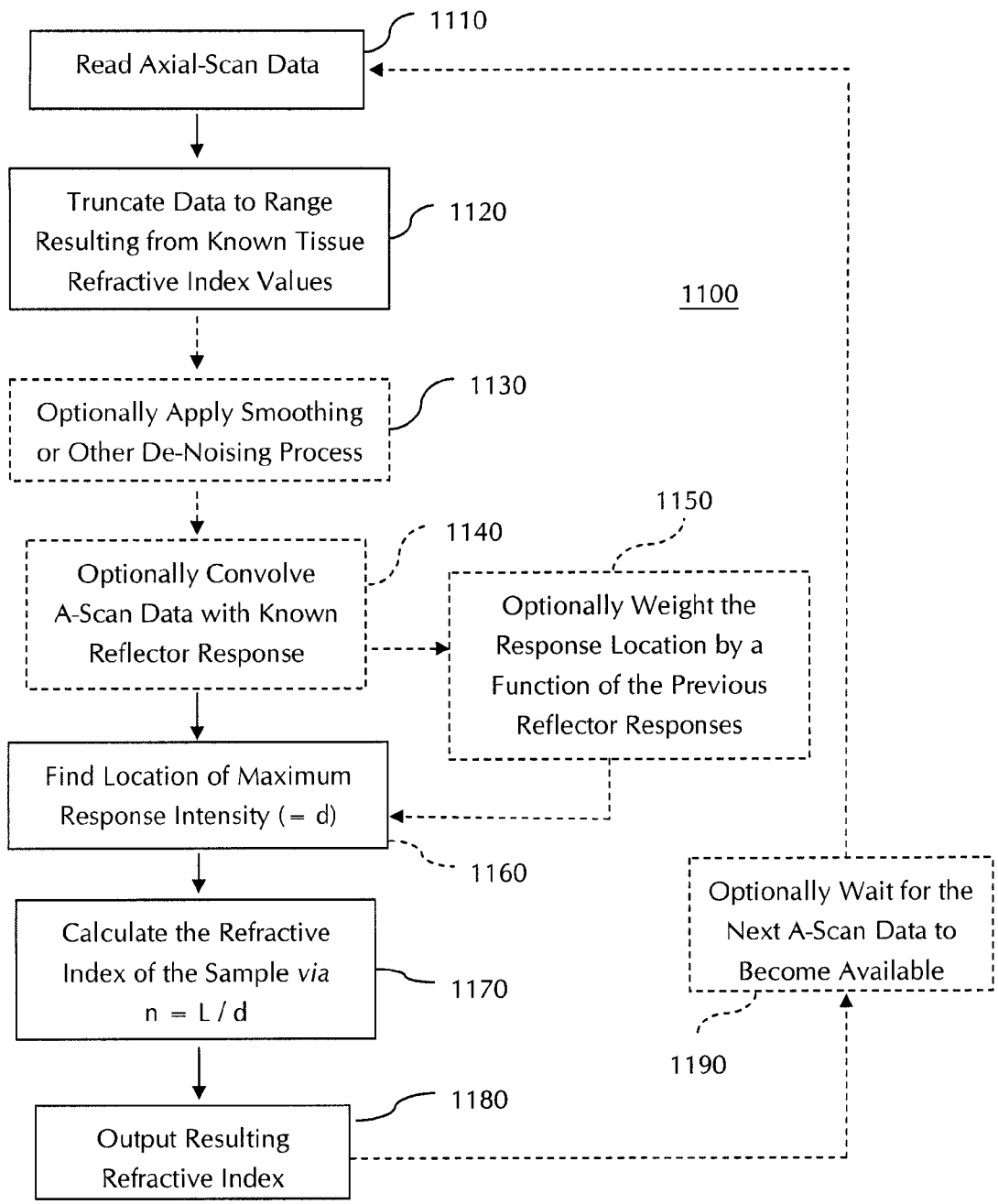
FIG. 11 depicts a flowchart of an example of a software system for determining a refractive index of tissue from a sample signal.

FIG. 11 represents a flow chart of an example of a computer program product, which includes computer readable program code, for determining a refractive index of tissue from a sample signal of radiation that has impinged upon the tissue. The computer program product begins by reading the axial scan data 1110 obtained by low-coherence interferometry. The axial scan data is then truncated to a range resulting from known tissue refractive index values 1120. This truncated data optionally may be subjected to smoothing or other de-noising processes 1130. Optionally the axial scan data may be convolved with the known reflector response 1140, and the response location optionally may be weighted by a function of the previous reflector responses 1150, if applicable. The location of maximum response intensity is then located 1160. This value of "d" is used to calculate the refractive index using Equation 1 (1170), and the output of the resulting refractive index is then produced 1180. The computer program product optionally may wait for the next axial scan data to become available 1190.

The following examples are provided to illustrate one or more preferred embodiments of the invention. Numerous variations may be made to the following examples that lie within the scope of the invention.

EXAMPLES

Example 1

Refractive Index Analysis By Low-Coherence Interferometry

A fiber-based low-coherence interferometer was used to measure the refractive indices of different types of tissue. A diode-pumped mode-locked titanium:sapphire laser source with a center wavelength around 780 nm was used as the optical source. This laser pumped an ultrahigh numerical aperture (UHNA4, Nufern) fiber to spectrally broaden the output bandwidth to 120 nm. Dispersion and polarization were matched in the interferometer arms. A precision linear optical scanner was used to scan the reference arm, and the small nonlinearity (less than 0.5%) was corrected by calibration. The axial resolution of this system was measured to be 3 µm in air. A high-speed (5 Mega-samples per second, 12-bit) analog-digital converter (NI-PCI-6110, National Instruments) was used to acquire interferometric fringe data. Axial scans containing the interferometric signals were sampled at 100,000 data points.

Samples of human breast tissue were placed on a reflective surface, and the reflective surface was positioned at a distance from the end of the optical fiber of the sample arm. The refractive index of each tissue was determined by measuring the distance from the end of the optical fiber to the reflective surface, and then calculating the refractive index according to Equation 1.

FIG. 12A is an OCT image of fat (adipose) tissue from a human breast, and FIG. 12B is an OCT image of invasive ductal carcinoma tissue from a human breast. These displaced reflector images also provided for refractive index calculations. See, for example, Tearney, G. J. et al., "Determination of the refractive index of highly scattering human tissue by optical coherence tomography", *Optics Letters*, 20(21), 2258-2260 (1995). The adipose tissue had a higher refractive index than did the carcinoma tissue.

FIG. 13A is a graph of the axial intensity as a function of scan depth in the adipose tissue, where the scan line was along the arrow in FIG. 12A. FIG. 13B is the same type of graph for the carcinoma tissue. Each of these axial intensity profiles had a depth-dependent decay in intensity, with the decay being more pronounced for the carcinoma tissue. The carcinoma tissue had a higher attenuation coefficient than did the adipose tissue.

The determined refractive index of breast tissue was from 1.27 to 1.33. The determined refractive index of fat was from 1.44 to 1.46, which compared well with published values of 1.44 to 1.53. The determined refractive index of invasive ductal carcinoma was 1.34 to 1.42. These results demonstrate that tissues commonly found in the breast may be distinguished based on refractive index, either alone or in combination with other optical properties.

Example 2

Optical Guidance of Biopsy Needle

A PinPoint® guiding introducer needle (Boston Scientific) is modified by replacing the piercing tip with a probe. The probe includes a housing having a piercing tip at the distal end, an optical fiber having an exposed end and an optical path extending from the exposed end, a gap, and a reflective surface positioned across the gap from the exposed end and within the optical path. See, for example, FIGS. 5-6. The width of the housing is 400 micrometers, and the width of the gap is 150 micrometers. The optical fiber is single-mode fiber N47A7AS3/1060 from Fiber Instrument Sales, Inc. (Oriskany, N.Y.), and is secured in a groove in the probe with an adhesive. The fiber is extended from the probe along the needle, and is optically coupled to a low-coherence interferometer system, such as those described in Example 1. Thus, the probe is a part of the sample arm of the interferometer. A GRIN lens is attached to the exposed end, and the reflective surface is positioned perpendicular to the optical path. The low-coherence interferometer is coupled to a visual display that displays the refractive index of the tissue being analyzed, as well as an identification of the tissue type.

The modified introducer needle is inserted into the breast of a patient, and the visual display is observed until tumor tissue is identified as being in contact with the probe. The modified introducer needle is removed, leaving the cannula in place. A Delta Cut® core biopsy needle (Boston Scientific) attached to an Easy Core™ biopsy device is inserted through the cannula of the introducer needle. The biopsy needle is activated to cut a sample of the tumor tissue, and then removed to retrieve the tissue sample. The modified introducer needle is inserted and repositioned until another tumor tissue is in contact with the probe, as indicated by the visual display. A biopsy needle is inserted through the cannula of the introducer needle, a sample of tumor tissue is cut, and the biopsy needle is removed. The location of tumor tissue and biopsy of tissue samples is repeated until the desired number of tissue samples is obtained.

While various embodiments of the invention have been described, it will be apparent to those of ordinary skill in the art that other embodiments and implementations are possible within the scope of the invention. Accordingly, the invention is not to be restricted except in light of the attached claims and their equivalents.

What is claimed is:

1. A method of analyzing tissue, comprising:
   inserting a probe into tissue;
   impinging radiation upon the tissue;
   obtaining a sample signal of the radiation from the tissue; and
   determining a refractive index of the tissue from the sample signal;
   wherein the probe comprises:
   a housing,
   a piercing tip, at a distal end of the housing,
   a groove, in the housing,
   a radiation source, and
   a radiation collector,
   wherein an optical path extends across the groove between the radiation source and the radiation collector.

2. The method of claim 1, further comprising determining at least one other optical property of the tissue.

3. The method of claim 2, where the at least one other optical property is selected from the group consisting of the attenuation coefficient, the scattering profile, the anisotropy factor, the birefringence, the spectral shift, and the texture.

4. The method of claim 1, where the impinging radiation comprises passing low-coherence radiation through an optical fiber to the tissue; and the determining comprises combining the sample signal with a reference signal to produce an interferogram.

5. The method of claim 1, where the radiation source comprises a first optical fiber having a first exposed end.

6. The method of claim 1, wherein the radiation source is a light-emitting diode.

7. The method of claim 1, wherein the radiation source is a laser device.

8. The method of claim 1, wherein the radiation collector comprises a second optical fiber having a second exposed end.

9. The method of claim 1, wherein the radiation collector comprises an electrooptic sensor.

10. The method of claim 8, wherein the obtaining the sample signal comprises collecting radiation that has been transmitted through the tissue from the radiation source to the second exposed end, and
the determining the refractive index comprises comparing a physical distance from the radiation source to the second exposed end and a measured pathlength from the radiation source to the second exposed end.

11. The method of claim 8, wherein the radiation source comprises a first optical fiber having a first exposed end,
the obtaining the sample signal comprises collecting radiation that has been transmitted through the tissue from the first exposed end to the second exposed end, and
the determining the refractive index comprises comparing a physical distance from the first exposed end to the second exposed end and a measured pathlength from the first exposed end to the second exposed end.

12. The method of claim 1, wherein the obtaining the sample signal comprises collecting radiation that has been transmitted through the tissue from the radiation source to the radiation collector, and
the determining the refractive index comprises measuring the angle of displacement of radiation that has been transmitted through the tissue from the radiation source to the radiation collector.

13. The method of claim 12, wherein the radiation collector comprises an electrooptic sensor.

14. The method of claim 1, further comprising identifying the tissue by the refractive index.

15. A method of performing a biopsy of tissue, comprising:
identifying tissue according to the method of claim 14; and
biopsying at least a portion of the tissue.

16. The method of claim 1, wherein the distance between the radiation source and radiation collector is 50 micrometers to 2.0 millimeters.

17. A method of analyzing tissue, comprising:
inserting a probe into tissue;
impinging radiation upon the tissue;
obtaining a sample signal of the radiation from the tissue; and
determining a refractive index of the tissue from the sample signal;
wherein the probe comprises:
a housing,
a piercing tip, at a distal end of the housing,
a groove, in the housing,
a radiation source, and
a reflective surface,
wherein an optical path extends across the groove between the radiation source and the reflective surface.

18. The method of claim 17, further comprising determining at least one other optical property of the tissue.

19. The method of claim 18, wherein the at least one other optical property is selected from the group consisting of the attenuation coefficient, the scattering profile, the anisotropy factor, the birefringence, the spectral shift, and the texture.

20. The method of claim 17, wherein the radiation source comprises a first optical fiber having a first exposed end.

21. The method of claim 17, wherein the radiation source is a light-emitting diode.

22. The method of claim 17, wherein the radiation source is a laser device.

23. The method of claim 20, wherein the obtaining the sample signal comprises collecting radiation that has been reflected from the reflective surface to the first exposed end, and
the determining the refractive index comprises comparing a physical distance from the first exposed end to the reflective surface and a measured pathlength from the first exposed end to the reflective surface.

24. The method of claim 17, further comprising a second optical fiber having a second exposed end,
wherein the obtaining the sample signal comprises collecting radiation that has been reflected from the reflective surface to the second exposed end, and
the determining the refractive index comprises comparing a physical distance from the second exposed end to the reflective surface and a measured pathlength from the second exposed end to the reflective surface.

25. The method of claim 17, wherein the obtaining the sample signal comprises collecting radiation that has been reflected from the reflective surface, and
the determining the refractive index comprises measuring the angle of displacement of radiation that has been reflected from the reflective surface.

26. The method of claim 25, wherein radiation is collected by an electrooptic sensor.

27. The method of claim 17, further comprising identifying the tissue by the refractive index.

28. The method of claim 17, wherein the distance between the radiation source and reflective surface is 50 micrometers to 2.0 millimeters.

* * * * *

UNITED STATES PATENT AND TRADEMARK OFFICE
CERTIFICATE OF CORRECTION

PATENT NO. : 7,787,129 B2
APPLICATION NO. : 11/669561
DATED : August 31, 2010
INVENTOR(S) : Adam M. Zysk et al.

It is certified that error appears in the above-identified patent and that said Letters Patent is hereby corrected as shown below:

TITLE PG, ITEM (56)
Other Publications:

Page 3:
Col. 1, line 69, please delete "In Vivo" and insert --*In Vivo*--
Col. 2, line 21, please delete "In vivo" and insert --*In vivo*--

Page 5:
Col. 1, line 53, please delete "In vivo" and insert --*In vivo*--
Col. 2, line 32, please delete "in vivo" and insert --*in vivo*--
Col. 2, line 60, please delete "In vitro" and insert --*In vitro*--

Page 6:
Col. 1, line 31, please delete "in vivo" and insert --*in vivo*--
Col. 1, line 40, please delete "in vivo" and insert --*in vivo*--

Page 7:
Col. 2, line 3, please delete "4-6" and insert --406--
Col. 2, lines 4-5, please delete "in vivo" and insert --*in vivo*--
Col. 2, line 9, please delete "in vivo" and insert --*in vivo*--
Col. 2, line 11, please delete "in vivo" and insert --*in vivo*--
Col. 2, line 43, please delete "in vivo" and insert --*in vivo*--
Col. 2, line 52, please delete "In vivo" and insert --*In vivo*--
Col. 2, line 55, please delete "in vivo" and insert --*in vivo*--

Page 8:
Col. 1, line 16, please delete "in vivo" and insert --*in vivo*--
Col. 1, line 28, please delete "in vivo" and insert --*in vivo*--
Col. 1, line 67, please delete "in vivo" and insert --*in vivo*--

Signed and Sealed this
Thirteenth Day of September, 2011

David J. Kappos
*Director of the United States Patent and Trademark Office*

CERTIFICATE OF CORRECTION (continued)
U.S. Pat. No. 7,787,129 B2

Col. 2, line 39, please delete "In vivo" and insert --*In vivo*--

Page 9:
Col. 1, line 9, please delete "in vivo" and insert --*in vivo*--
Col. 2, line 32, please delete "et al'" and insert --et al.--

Page 10:
Col. 1, line 63, please delete "4-6" and insert --406--
Col. 1, lines 64-65, please delete "in vivo" and insert --*in vivo*--
Col. 1, line 69, please delete "in vivo" and insert --*in vivo*--
Col. 1, line 71, please delete "in vivo" and insert --*in vivo*--
Col. 2, line 30, please delete "in vivo" and insert --*in vivo*--
Col. 2, line 39, please delete "in vivo" and insert --*in vivo*--
Col. 2, line 42, please delete "in vivo" and insert --*in vivo*--

Page 11:
Col. 1, line 3, please delete "in vivo" and insert --*in vivo*--
Col. 1, line 3, please delete "imaigng" and insert --imaging--
Col. 1, line 15, please delete "in vivo" and insert --*in vivo*--
Col. 1, line 54, please delete "in vivo" and insert --*in vivo*--
Col. 1, line 63, please delete "$B^{1\pi}_{u}$" and insert --$B^{1}\pi_{u}$--
Col. 2, line 26, please delete "In vivo" and insert --*In vivo*--
Col. 2, line 69, please delete "in vivo" and insert --*in vivo*--

Page 12:
Col. 2, line 62, please delete "Chol'" and insert --Choi--

Page 13:
Col. 1, line 7, please delete "60791 D-1" and insert --60791D-1--